(12) United States Patent
Craik et al.

(10) Patent No.: US 7,592,433 B1
(45) Date of Patent: Sep. 22, 2009

(54) POLYNUCLEOTIDES ENCODING CYCLOTIDE-LIKE STRUCTURES

(75) Inventors: David James Craik, Chapel Hill (AU); Marilyn Anne Anderson, Keilor (AU); Cameron Victor Jennings, Doncaster (AU)

(73) Assignee: The University of Queensland; Hexima Limited (AU)

( * ) Notice: Subject to any disclaimer, the term of this patent is extended or adjusted under 35 U.S.C. 154(b) by 270 days.

(21) Appl. No.: 10/129,201

(22) PCT Filed: Nov. 3, 2000

(86) PCT No.: PCT/AU00/01352

§ 371 (c)(1),
(2), (4) Date: Sep. 10, 2002

(87) PCT Pub. No.: WO01/34829

PCT Pub. Date: May 17, 2001

(30) Foreign Application Priority Data

Nov. 5, 1999 (AU) .................................... PQ3884
Nov. 25, 1999 (AU) .................................... PQ4235

(51) Int. Cl.
*C07H 21/04* (2006.01)
*C07K 14/00* (2006.01)

(52) U.S. Cl. ...................... 536/23.1; 530/317; 530/300; 530/350; 435/252.1; 435/235.1; 435/69.7; 435/320.1

(58) Field of Classification Search ................ 536/23.1; 514/9, 12; 530/317, 300, 334, 335, 344, 530/370, 350; 435/320.1, 69.7, 235.1, 252.1
See application file for complete search history.

(56) References Cited

U.S. PATENT DOCUMENTS 5,739,307 A * 4/1998 Johnson et al. .......... 536/23.51
6,573,363 B1 * 6/2003 Sheppard et al. ............ 530/350

FOREIGN PATENT DOCUMENTS

WO    WO 00/68265    11/2000

OTHER PUBLICATIONS

Craik et al., "Plant Cyclotides: A Unique Family of Cyclic and Knotted Proteins that Defines the Cyclic Cystine Knot Structural Motif," *J. Mol. Biol.*, Dec. 17, 1999, pp. 1327-1336, vol. 294, No. 5, Academic Press, Australia.

Daly et al., "Acyclic Permutants of Naturally Occuring Cyclic Proteins," *J. Mol. Biol.*, Jun. 23, 2000, pp. 19068-19075, vol. 275, No. 25, United States of America.
Daly et al., "Chemical Synthesis and Folding Pathways of Large Cyclic Polypeptides: Studies of the Cystine Knot Polypeptide Kalata B1," *Biochemistry*, Aug. 10, 1999, pp. 10606-10614, vol. 38, No. 32, published on Web Jul. 21, 1999, © American Chemical Society.
Saether et al., "Elucidation of the Primary and Three-Dimensional Structure of the Uterotonic Polypeptide Kalata B1," *Biochemistry*, Apr. 4, 1995, pp. 4147-4158, vol. 34, No. 13, © 1995 American Chemical Society, United States of America.
Tam et al., "An Unusual Structural Motif of Antimicrobial Ppeptides Containing End-to-End Macrocyle and Cystine-Knot Disulfides," *Proc. Nat'l. Acad. Sci.*, Aug. 3, 1999, pp. 8913-8918, vol. 96, No. 16, United States of America.
Pallaghy et al., "A common structural motif incorporation a cystine knot and a triple-stranded β-sheet in toxic and inhibitory polypeptides," *Protein Science*, Oct. 1994, pp. 1833-1839, vol. 3, No. 10, Cambridge University Press, United States of America.
International Search Report from International Application PCT/AU00/01352 dated Feb. 28, 2001.
Jennings, C., et al., "Biosynthesis and Insecticidal Properties of Plant Cyclotides: The Cyclic Knotted Proteins from *Oldenlandia affinis*," *Proceedings of the National Academy of Sciences of the United States of America*, 2001, pp. 10614-10619, vol. 98, No. 19.
Martinez-Bueno, M., et al., "Determination of the Gene Sequence and the Molecular Structure of the Enterococcal Peptide Antibiotic AS-48," *J, Bacteriology*, 1994, pp. 6334-6339, vol. 176, No. 20.
Tang, Y., et al., "A Cyclic Antimicrobial Peptide Produced in Primate Leukocytes by the Ligation of Two Truncated Alpha-Defensis," *Science*, 1999, pp. 498-502, vol. 285, No. 5439.
Gran, L., et al., "A plant containing uteroactive peptides used in African traditional medicine," *Journal of Ethnopharmacology*, 2000, pp. 197-203, vol. 70.
Solbiati, J., et al., "Sequence Analysis of the Four Plasmid Genes Required To Produce the Curcular Peptide Antibiotic Microcin J25," *Journal of Bacteriology*, Apr. 1999, pp. 2659-2662, vol. 181, No. 8.

* cited by examiner

*Primary Examiner*—Chih-Min Kam
(74) *Attorney, Agent, or Firm*—Casimir Jones, S.C.

(57) ABSTRACT

The present invention relates to a novel nucleic acid molecule encoding an amino acid sequence, which is capable of forming a cyclic structure. Cyclization may occur within a cell or cell membrane, or linear forms of the molecules may be circularised or partially circularised, in vitro using isolated enzyme systems or chemical means. The cyclised amino acid sequence is generally in the form of a stabilized folded structure such as a cyclic knotted peptide, polypeptide or protein or functional equivalent. The nucleic acid molecules and cyclic and linear peptides are useful inter alia in the generation of molecules having animal or plant therapeutic properties, as well as in a range of diagnostic, industrial and agricultural, including horticultural, applications. Of particular importance is the use of these molecules in the protection of plants, such as crop plants, from pest and/or pathogen infestation.

5 Claims, 25 Drawing Sheets

|  |  |
|---|---|
| Primer Kal1 | <u>BamH1</u>.<br>CGGGATCCACICCIGGITGYACITG |
| Protein sequence |              T    P    G    C    T    C |
| Primer Kal2 | <u>BamH1</u>.<br>GGGGATCCGTITGYGGIGARACITG |
| Protein sequence |              V    C    G    E    T    C |
| Oligo-dT-HindIII | <u>HindIII</u>.<br>CGAAGCTTTTTTTTTTTTTTTTT |

```
        10         20         30         40         50
         |          |          |          |          |
GGATCCGTGTGCGGGGAGACGTGTGTTGGGGGAACTTGCAACACTCCAGG
  V  C  G  E  T  C  V  G  G  T  C  N  T  P  G 60         70         80         90        100
         |          |          |          |          |
CTGCACTTGCTCCTGGCCTGTTTGCACACGCAATGGCCTTCCTAGTTTGG
  C  T  C  S  W  P  V  C  T  R  N  G  L  P  S  L 110        120        130        140        150
         |          |          |          |          |
CCGCATAAtttgcttgatcaaactgcaaaaatgaatgagaaggccgacac
  A  A  *

160        170        180        190        200
         |          |          |          |          |
caataaagctatcaatgtagttggtccctgtacttaatttggttggctcc 210        220        230        240        250
         |          |          |          |          |
aaaccatgtgtgctgctcttgttttgttttttcttttttcttctctctt 260        270        280        290        300
         |          |          |          |          |
tcgggcactcttcaggacatgaagtgatgatcagtactctttgctatcat 310        320        330        340        350
         |          |          |          |          |
gttttctgtgcacaccttctattgtaggtgttgttgtgatgttgatgccc 360        370        380        390        400
         |          |          |          |          |
aattggaataaactgttgtcgttgttaaaaaaaaaaaaaaaaaaaaaaa 410
         |
aaaaaaaagcttcg
```

Figure 2

A 2604 —
1383 —
955 —
623 —
281 —
B 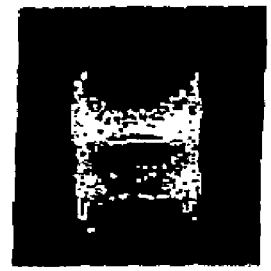
Figure 3

TTCGGCA

CCAGCACTTTCTTAAAATTTACTGCTTTTTCTTATTTCTTGTTCTGTGCTTGCTTCTTCC

```
            10        20        30        40        50        60
            |         |         |         |         |         |
ATGGCTAAGTTCACCGTCTGTCTCCTCCTGTGCTTGCTTCTTGCAGCATTTGTTGGGGCG
 M  A  K  F  T  V  C  L  L  L  C  L  L  L  A  A  F  V  G  A
 |                          |
-20                        -10
```

```
            70        80        90       100       110       120
            |         |         |         |         |         |
TTTGGATCTGAGCTTTCTGACTCCCACAAGACCACCTTGGTCAATGAAATCGCTGAGAAG
 F  G  S  E  L  S  D  S  H  K  T  T  L  V  N  E  I  A  E  K
 |                          |                               |
 1                         10                              20
```

```
           130       140       150       160       170       180
            |         |         |         |         |         |
ATGCTACAAAGAAAGATATTGGATGGAGTGGAAGCTACTTTGGTCACTGATGTCGCCGAG
 M  L  Q  R  K  I  L  D  G  V  E  A  T  L  V  T  D  V  A  E
                            |                               |
                           30                              40
```

```
           190       200       210       220       230       240
            |         |         |         |         |         |
AAGATGTTCCTAAGAAAGATGAAGGCTGAAGCGAAAACTTCTGAAACCGCCGATCAGGTG
 K  M  F  L  R  K  M  K  A  E  A  K  T  S  E  T  A  D  Q  V
                            |                               |
                           50                              60
```

```
           250       260       270       280       290       300
            |         |         |         |         |         |
TTCCTGAAACAGTTGCAGCTCAAAGGACTTCCAGTATGCGGTGAGACTTGTGTTGGGGA
 F  L  K  Q  L  Q  L  K  G  L  P  V  C  G  E  T  C  V  G
                            |                               |
                           70                              80
```

```
           310       320       330       340       350       360
            |         |         |         |         |         |
ACTTGCAACACTCCAGGCTGCACTTGCTCCTGGCCTGTTTGCACACGCAATGGCCTTCCT
 T  C  N  T  P  G  C  T  C  S  W  P  V  C  T  R  N  G  L  P
                            |                               |
                           90                             100
```

Figure 4

```
                370         380         390         400         410        42
                 |           |           |           |           |          |
         AGTTTGGCCGCATAATTTGCTTGATCAAACTGCAAAAATGAATGAGAAGGCCGACACCAA
            S    L    A    A    *
                            |
                           104

430         440         450         460         470       480
                 |           |           |           |           |          |
         TAAAGCTATCAATGTAGTTGGTCCCTGTACTTAATTTGGTTGGCTCCAAACCATGTGTGC 490         500         510         520         530       540
                 |           |           |           |           |          |
         TGCTCTTGTTTTTGTTTTTTCTTTTTTCTTCTCTCTTTCGGGCACTCTTCAGGACATGAA 550         560         570         580         590       600
                 |           |           |           |           |          |
         GTGATGATCAGTACTCTTTGCTATCATGTTTTCTGTGCACACCTTCTATTGTAGGTGTTG 610         620         630         640         650       660
                 |           |           |           |           |          |
         TTGTGATGTTGATGCCCAATTGGAATAAACTGTTGTCGTTGTTAAAAAAAAAAAAAAAAA
```

Figure 4 (continued)

```
              GCACGAGAAACAATATCTAATAATTACTTTGATTTCTTGAGAAATTTGATCTTCC 10         20         30         40         50         60
          |          |          |          |          |          |
     ATGGCTAAGTTCACCAAGTCTCTCGTCCTGTGCTTGCTTCTTGCAGCTTTTGTTGGGGCT
        M  A  K  F  T  K  S  L  V  L  C  L  L  L  A  A  F  V  G  A
        |                             |
       -20                           -10

70         80         90        100        110        120
          |          |          |          |          |          |
     TTCGGAGCTGAGCTTTCTGAAGCTGACAAAGCCAACGTGGTCAATGAAATCGCTGCCAAT
        F  G  A  E  L  S  E  A  D  K  A  N  V  V  N  E  I  A  A  N
        |                             |                             |
        1                            10                            20

130        140        150        160        170        180
          |          |          |          |          |          |
     ATTCAACGAGAGATACTGAAGGGAGTGAAAAGTTCAGAAACCACCCTTACCATGTTCCTG
        I  Q  R  E  I  L  K  G  V  K  S  S  E  T  T  L  T  M  F  L
                                       |                             |
                                      30                            40

190        200        210        220        230        240
          |          |          |          |          |          |
     AAAGAGATGCAGCTCAAAGGTCTTCCAACATGTGGTGAGACTTGCTTTGGGGGAACTTGC
        K  E  M  Q  L  K  G  L  P  T  C  G  E  T  C  F  G  G  T  C
                              |
                             50                                    60

250        260        270        280        290        300
          |          |          |          |          |          |
     AACACTCCTGGATGCAGTTGCTCCTCCTGGCCGATTTGCACTCGCAATGGCCTTCCTAAG
        N  T  P  G  C  S  C  S  S  W  P  I  C  T  R  N  G  L  P  K
                                       |
                                      70                            80

310        320        330        340        350        360
          |          |          |          |          |          |
     AGGGCTGGAGTGAAAAGTTCAGAAACCACCCTTACCATGTTCCTGAAAGAGATGCAGCTC
        R  A  G  V  K  S  S  E  T  T  L  T  M  F  L  K  E  M  Q  L
                       |                                              |
                      90                                            100
```

Figure 5

```
              370        380        390        400        410        420
               |          |          |          |          |          |
AAAGGTCTTCCAACATGTGGTGAGACTTGCTTTGGGGGAACTTGCAACACTCCTGGATGC
  K   G  L  P  T  C  G  E  T  C  F  G  G  T  C  N  T  P  G  C
                              |                              |
                             110                            120

430        440        450        460        470        480
               |          |          |          |          |          |
ACTTGCGATCCCTGGCCGATTTGCACACGCGATGGCCTTCCTAGTGCGGCCGCATAATTT
  T  C  D  P  W  P  I  C  T  R  D  G  L  E    S  A  A  A  *
                              |                              |
                             130                            138

490        500        510        520        530        540
               |          |          |          |          |          |
GCTCGATCAAACTGGAAAAATGAATAAGAAGGGACACCAATAAAGCTATGAACGCTGTTG 550        560        570        580        590        600
               |          |          |          |          |          |
GTCCCAGTGTATCTGTTGATTTGGTTGGCTCCAAACCATATGTGCTGCTTGTTTTTTTTT 610        620        630        640        650        660
               |          |          |          |          |          |
CTTTTTTCTTTTCTCTTTCGGGCACTCTTCATGACATGAAGAGATCATGATGACTCTTTG 670        680        690        700        710        720
               |          |          |          |          |          |
TTATTATGTTTTCTGTGCACACCTTCCCCTGTACGTAGGTGTGGTTCACATGTTATTGCC 730        740        750        760        770        780
               |          |          |          |          |          |
CGAATGGAATAAATTGTGGTTGTCGTTGTTATCGTACTCTCTATTTTAAATTCAAAAAAA

788
   |
AAAAAAAA
```

Figure 5 (continued)

```
                                                              AATTCGGCAG
      GAGCTTCTTATAATTTTACTGCTTTTCTTATTTCTAGAGAAAGGAGAAATTCGATCTTCC 10        20        30        40        50        60
               |         |         |         |         |         |
      ATGGCTAAGTTCACCAACTGTCTCGCCCTGTGCTTGCTTCTTGCAGCAGTTGTTGGGGCT
       M  A  K  F  T  N  C  L  A  L  C  L  L  L  A  A  V  V  G  A
       |                             |
      -20                           -10

70        80        90       100       110       120
               |         |         |         |         |         |
      TTCGGAGTTGAGCTTTCTGAAGCCGACAAGAGCGCCGTGGTCAATGAAATCGCTGAGAAG
      ↑F  G  V  E  L  S  E  A  D  K  S  A  V  V  N  E  I  A  E  K
       ||                            |                            |
       1                            10                           20

130       140       150       160       170       180
               |         |         |         |         |         |
      ATGGCCCTACAGGAGATGCTGGACGGAGTCGACAAGCTGTTCCTGAGGAAGATGAAAAGC
       M  A  L  Q  E  M  L  D  G  V  D  K  L  F  L  R  K  M  K  S
                                    |                            |
                                   30                           40

190       200       210       220       230       240
               |         |         |         |         |         |
      TCTGAAACCACCCTCACCATGTTCCTGAAAGAGATGCAGCTCAAAGGTCTTCCAGTCTGC
       S  E  T  T  L  T  M  F  L  K  E  M  Q  L  K ↑G ↑L ↑P ↑V  C
                                    |                            |
                                   50                           60

250       260       270       280       290       300
               |         |         |         |         |         |
      GGTGAGACTTGCACTTTGGGAACTTGCTATACTCAAGGCTGCACTTGCTCCTGGCCTATC
       G  E  T  C  T  L  G  T  C  Y  T  Q  G  C  T  C  S  W  P  I
                                    |                            |
                                   70                           80

310       320       330       340       350       360
               |         |         |         |         |         |
      TGCAAGCGCAATGGCCTTCCTGATGTGGCCGCATAATTTGCTCGATCAAAAACTGCAGAA
       C  K  R  N ↑G ↑L ↑P ↑D  V  A  A  *
                                    |
                                   91
```

Figure 6

```
        370       380       390       400       410       420
         |         |         |         |         |         |
ATGAATAAGAAGGGATACCAAATAATGCTATGAATATTGTTGGTCCCTGTGTCTGTTGAT
        430       440       450       460       470       480
         |         |         |         |         |         |
TTGGTTGGCTAGCTCCGAACCATATGTTCTGCTTGTGTTTTCGTTTTGTTTTCTCTTT
        490       500       510       520       530       540
         |         |         |         |         |         |
TGGGCACTCTTCATATGACATAAAGAGATCTTGGATCTGATATTGGTCACATGTTAATAC
        550       560       570       580       592
         |         |         |         |         |
CCAATTTCAAAAAATCGTTGTTATCGTTGTCATTAAAAAAAAAAAAAAAAAA
```

Figure 6 (continued)

```
                                        AATTCGGCACCAGATACAACCCCT
TTCTTATAATTTATTGCTTTTCTTATTCCTTGAAAAAGGAGAAATAATATTGGATCTTCC 10        20        30        40        50        60
         |         |         |         |         |         |
ATGGCTAAGTTCACCAACTGTCTCGTCCTGAGCTTGCTTCTAGCAGCATTTGTTGGGGCT
  M   A   K   F   T   N   C   L   V   L   S   L   L   A   A   F   V   G   A
  |                                       |
 -20                                      -10

70        80        90       100       110       120
         |         |         |         |         |         |
TTCGGAGCTGAGTTTTCTGAAGCCGACAAGGCCACCTTGGTCAATGATATCGCTGAGAAT
  F   G   A   E   F   S   E   A   D   K   A   T   L   V   N   D   I   A   E   N
  |                                   |                                       |
  1                                  10                                      20

130       140       150       160       170       180
         |         |         |         |         |         |
ATCCAAAAAGAGATACTGGGCGAAGTGAAGACTTCTGAAACCGTCCTTACGATGTTCCTG
  I   Q   K   E   I   L   G   E   V   K   T   S   E   T   V   L   T   M   F   L
                                      |_____|
                                      30                                         40

190       200       210       220       230       240
         |         |         |         |         |         |
AAAGAGATGCAGCTCAAAGGTCTTCCAGTATGCGGCGAGACTTGCTTTGGGGGAACTTGC
  K   E   M   Q   L   K   G   L   P   V   C   G   E   T   C   F   G   G   T   C
 |_____↑                                       |
                    50                                      60

250       260       270       280       290       300
         |         |         |         |         |         |
AACACTCCAGGCTGCTCTTGCACCTGGCCTATCTGCACACGCGATAGCCTTCCTATGAGG
  N   T   P   G   C   S   C   T   W   P   I   C   T   R   D ↑ S   L   P   M   R
                              |                                                 |
                             70                                                80
```

Figure 7

```
       310        320        330        340        350        360
        |          |          |          |          |          |
GCTGGAGGAAAAACATCTGAAACCACCCTTCATATGTTCCTGAAAGAGATGCAGCTCAAG
  A  G  G  K  T  S  E  T  T  L  H  M  F  L  K  E  M  Q  L  K
                              |                                |
                              90                              100

370        380        390        400        410        420
        |          |          |          |          |          |
GGTCTTCCAGTTTGCGGCGAGACTTGCTTTGGGGGAACTTGCAACACTCCAGGCTGCTCG
 ↑G  L  P  V  C  G  E  T  C  F  G  G  T  C  N  T  P  G  C  S
                              |                                |
                             110                              120

430        440        450        460        470        480
        |          |          |          |          |          |
TGCACCTGGCCTATCTGCACACGCGATAGCCTTCCTATGAGTGCTGGAGGAAAAACATCT
  C  T  W  P  I  C  T  R  D↑ S  L  P  M  S  A  G  G  K  T  S
                              |                                |
                             130                              140

490        500        510        520        530        540
        |          |          |          |          |          |
GAAACCACCCTTCATATGTTCCTGAAAGAGATGCAGCTCAAGGGTCTTCCAGTTTGCGGC
  E  T  T  L  H  M  F  L  K  E  M  Q  L  K↑ G  L  P  V  C  G
                              |                                |
                             150                              160

550        560        570        580        590        600
        |          |          |          |          |          |
GAGACTTGCTTTGGGGGAACTTGCAACACTCCAGGCTGCTCGTGCACCTGGCCTATATGC
  E  T  C  F  G  G  T  C  N  T  P  G  C  S  C  T  W  P  I  C
                              |                                |
                             170                              180

610        620        630        640        650        660
        |          |          |          |          |          |
ACACGTGATAGCCTTCCTCTTGTGGCTGCATAATTTGCTTCATCAAACTGCAAAATGAAT
  T  R  D↑ S  L  P  L  V  A  A  *
                 |
                190

670        680        690        700        710        720
        |          |          |          |          |          |
AAGAAGGGACACTAAATTAGCTATGAATTTTGTTGGCCCTTGTGTCTGGTAATTTGGTTC
```

Figure 7 (continued)

```
          730       740       750       760       770       780
           |         |         |         |         |         |
CCGCCAAATTAACCATATGTATGCATTGCTCCTTTTTTCTTTCTTTTTTTTCCCCCTCAT 790       800       810       820       830       840
           |         |         |         |         |         |
TTGGGCACTCTTCATTACATGAAGAGATCATGACGCTTTGTTACTCTGAGCACCCCTGT 850       860       870       880       890       900
           |         |         |         |         |         |
TGGTGTTGTTCACATGTTNATGCCCATGTTGGAATAAACTCTTGTTTTTGTTACCAAAAA

914
           |
AAAAAAAAAAAAAA
```

Figure 7 (continued)

*Oa*K 1
*Oa*K 2
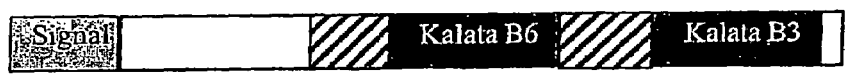
*Oa*K 3
*Oa*K 4
Figure 8A

B1: KTSETADQVFLKQLQLK GLP VCGETCVGGTCNTPGCTCS-WPVCTRN GLP SLAA
B2: KTSETVLTMFLKEMQLK GLP VCGETCFGGTCNTPGCSCT-WPICTRD SLP LVAA
B3: KSSETTLTMFLKEMQLK GLP TCGETCFGGTCNTPGCTCDPWPICTRD GLP SAAA
B6: KSSETTLTMFLKEMQLK GLP TCGETCFGGTCNTPGCSCSSWPICTRN GLP ----
B7: KSSETTLTMFLKEMQLK GLP VCGETCTLGTCYTQGCTCS-WPICKRN GLP VAA

B1, B3, B6, B7: GLP - Cyclotide - GLP

B2: GLP - Cyclotide - SLP

Figure 8B

*Viola odorata* cyclotide sequence

```
        10         20         30         40         50         60
        |          |          |          |          |          |
GTGTGTGGGG AGACGTGCGT TGGTGGAACC TGTAACACCC CTGGGTGCTC TTGCAGCTGG
 V  C  G   E  T  C  V  G  G  T   C  N  T  P   G  C  S   C  S  W 70         80         90        100        110        120
        |          |          |          |          |          |
CCTGTTTGCA CCAGAAACTC TCTTGCCATG TAAGGCTGAG ATTTAGGCAA TGCTCAGATT
 P  V  C   T  R  N  S   L  A  M  *

130        140        150        160        170        180
        |          |          |          |          |          |
TGTTGTTTCT CGTTCTCGTT CTGGTTCTGG TTCTCATTAT CGTTATTGTT CTTGAGGAGA 190        200        210        220        230        240
        |          |          |          |          |          |
GGAGGCTATA CATGCTCGTG ACATGAAATT AGCAAAAAGT AAAATGTCAA GCATGCCTCC 250        260        270        280        290        300
        |          |          |          |          |          |
TCTTCCCTTC CTTTCTGTTT GAATTAATAA AAGTCCAGTT AATTATTTGT GCTAAAAAAA

311
        |
AAAAAAAAAA A
```

Figure 15

SEQUENCE LISTING

<160> NUMBER OF SEQ ID NOS: 40

<210> SEQ ID NO 1
<211> LENGTH: 67
<212> TYPE: DNA
<213> ORGANISM: Oldenlandia affinis

<400> SEQUENCE: 1
ttcggcacca gcactttctt aaaatttact gcttttcctt atttcttgtt ctgtgcttgc    60
ttcttcc    67

<210> SEQ ID NO 2
<211> LENGTH: 60
<212> TYPE: DNA
<213> ORGANISM: Oldenlandia affinis
<220> FEATURE:
<221> NAME/KEY: CDS
<222> LOCATION: (1)...(60)

<400> SEQUENCE: 2 atg gct aag ttc acc gtc tgt ctc ctc ctg tgc ttg ctt ctt gca gca    48
Met Ala Lys Phe Thr Val Cys Leu Leu Leu Cys Leu Leu Leu Ala Ala
 1               5                  10                  15 ttt gtt ggg gcg                                                    60
Phe Val Gly Ala
            20

<210> SEQ ID NO 3
<211> LENGTH: 20
<212> TYPE: PRT
<213> ORGANISM: Oldenlandia affinis

<400> SEQUENCE: 3

Met Ala Lys Phe Thr Val Cys Leu Leu Leu Cys Leu Leu Leu Ala Ala
 1               5                  10                  15

Phe Val Gly Ala
            20

<210> SEQ ID NO 4
<211> LENGTH: 312
<212> TYPE: DNA
<213> ORGANISM: Oldenlandia affinis
<220> FEATURE:
<221> NAME/KEY: CDS
<222> LOCATION: (1)...(312)

<400> SEQUENCE: 4 ttt gga tct gag ctt tct gac tcc cac aag acc acc ttg gtc aat gaa    48
Phe Gly Ser Glu Leu Ser Asp Ser His Lys Thr Thr Leu Val Asn Glu
 1               5                  10                  15 atc gct gag aag atg cta caa aga aag ata ttg gat gga gtg gaa gct    96
Ile Ala Glu Lys Met Leu Gln Arg Lys Ile Leu Asp Gly Val Glu Ala
                20                  25                  30 act ttg gtc act gat gtc gcc gag aag atg ttc cta aga aag atg aag   144
Thr Leu Val Thr Asp Val Ala Glu Lys Met Phe Leu Arg Lys Met Lys
            35                  40                  45 gct gaa gcg aaa act tct gaa acc gcc gat cag gtg ttc ctg aaa cag   192
Ala Glu Ala Lys Thr Ser Glu Thr Ala Asp Gln Val Phe Leu Lys Gln
        50                  55                  60 ttg cag ctc aaa gga ctt cca gta tgc ggt gag act tgt gtt ggg gga   240
Leu Gln Leu Lys Gly Leu Pro Val Cys Gly Glu Thr Cys Val Gly Gly
65                  70                  75                  80

```
act tgc aac act cca ggc tgc act tgc tcc tgg cct gtt tgc aca cgc      288
Thr Cys Asn Thr Pro Gly Cys Thr Cys Ser Trp Pro Val Cys Thr Arg
                85                  90                  95 aat ggc ctt cct agt ttg gcc gca                                      312
Asn Gly Leu Pro Ser Leu Ala Ala
            100
```

<210> SEQ ID NO 5
<211> LENGTH: 104
<212> TYPE: PRT
<213> ORGANISM: Oldenlandia affinis

<400> SEQUENCE: 5

```
Phe Gly Ser Glu Leu Ser Asp Ser His Lys Thr Thr Leu Val Asn Glu
 1               5                  10                  15

Ile Ala Glu Lys Met Leu Gln Arg Lys Ile Leu Asp Gly Val Glu Ala
             20                  25                  30

Thr Leu Val Thr Asp Val Ala Glu Lys Met Phe Leu Arg Lys Met Lys
         35                  40                  45

Ala Glu Ala Lys Thr Ser Glu Thr Ala Asp Gln Val Phe Leu Lys Gln
     50                  55                  60

Leu Gln Leu Lys Gly Leu Pro Val Cys Gly Glu Thr Cys Val Gly Gly
 65                  70                  75                  80

Thr Cys Asn Thr Pro Gly Cys Thr Cys Ser Trp Pro Val Cys Thr Arg
                85                  90                  95

Asn Gly Leu Pro Ser Leu Ala Ala
            100
```

<210> SEQ ID NO 6
<211> LENGTH: 288
<212> TYPE: DNA
<213> ORGANISM: Oldenlandia affinis

<400> SEQUENCE: 6

```
taatttgctt gatcaaactg caaaaatgaa tgagaaggcc gacaccaata aagctatcaa     60
tgtagttggt ccctgtactt aatttggttg gctccaaacc atgtgtgctg ctcttgtttt    120
tgttttttct tttttcttct ctctttcggg cactcttcag acatgaagt gatgatcagt     180
actctttgct atcatgtttt ctgtgcacac cttctattgt aggtgttgtt gtgatgttga    240
tgcccaattg gaataaactg ttgtcgttgt taaaaaaaa  aaaaaaaa                  288
```

<210> SEQ ID NO 7
<211> LENGTH: 105
<212> TYPE: DNA
<213> ORGANISM: Oldenlandia affinis
<220> FEATURE:
<221> NAME/KEY: CDS
<222> LOCATION: (7)...(105)

<400> SEQUENCE: 7

```
ggatcc gtg tgc ggg gag acg tgt gtt ggg gga act tgc aac act cca       48
       Val Cys Gly Glu Thr Cys Val Gly Gly Thr Cys Asn Thr Pro
        1               5                  10 ggc tgc act tgc tcc tgg cct gtt tgc aca cgc aat ggc ctt cct agt      96
Gly Cys Thr Cys Ser Trp Pro Val Cys Thr Arg Asn Gly Leu Pro Ser
 15                  20                  25                  30 ttg gcc gca                                                         105
Leu Ala Ala
```

```
<210> SEQ ID NO 8
<211> LENGTH: 33
<212> TYPE: PRT
<213> ORGANISM: Oldenlandia affinis

<400> SEQUENCE: 8

Val Cys Gly Glu Thr Cys Val Gly Gly Thr Cys Asn Thr Pro Gly Cys
 1               5                  10                  15

Thr Cys Ser Trp Pro Val Cys Thr Arg Asn Gly Leu Pro Ser Leu Ala
            20                  25                  30

Ala

<210> SEQ ID NO 9
<211> LENGTH: 309
<212> TYPE: DNA
<213> ORGANISM: Oldenlandia affinis

<400> SEQUENCE: 9
taatttgctt gatcaaactg caaaaatgaa tgagaaggcc gacaccaata aagctatcaa      60
tgtagttggt ccctgtactt aatttggttg gctccaaacc atgtgtgctg ctcttgtttt     120
tgttttttct ttttttcttct ctctttcggg cactcttcag acatgaagt gatgatcagt    180 actctttgct atcatgtttt ctgtgcacac cttctattgt aggtgttgtt gtgatgttga     240
tgcccaattg gaataaactg ttgtcgttgt taaaaaaaaa aaaaaaaaaa aaaaaaaaaa     300
aaagcttcg                                                             309

<210> SEQ ID NO 10
<211> LENGTH: 55
<212> TYPE: DNA
<213> ORGANISM: Oldenlandia affinis

<400> SEQUENCE: 10
gcacgagaaa caatatctaa taattacttt gatttcttga gaaatttgat cttcc          55

<210> SEQ ID NO 11
<211> LENGTH: 60
<212> TYPE: DNA
<213> ORGANISM: Oldenlandia affinis
<220> FEATURE:
<221> NAME/KEY: CDS
<222> LOCATION: (1)...(60)

<400> SEQUENCE: 11 atg gct aag ttc acc aag tct ctc gtc ctg tgc ttg ctt ctt gca gct      48
Met Ala Lys Phe Thr Lys Ser Leu Val Leu Cys Leu Leu Leu Ala Ala
 1               5                  10                  15 ttt gtt ggg gct                                                       60
Phe Val Gly Ala
            20

<210> SEQ ID NO 12
<211> LENGTH: 20
<212> TYPE: PRT
<213> ORGANISM: Oldenlandia affinis

<400> SEQUENCE: 12

Met Ala Lys Phe Thr Lys Ser Leu Val Leu Cys Leu Leu Leu Ala Ala
 1               5                  10                  15

Phe Val Gly Ala
            20
```

<210> SEQ ID NO 13
<211> LENGTH: 414
<212> TYPE: DNA
<213> ORGANISM: Oldenlandia affinis
<220> FEATURE:
<221> NAME/KEY: CDS
<222> LOCATION: (1)...(414)

<400> SEQUENCE: 13

```
ttc gga gct gag ctt tct gaa gct gac aaa gcc aac gtg gtc aat gaa      48
Phe Gly Ala Glu Leu Ser Glu Ala Asp Lys Ala Asn Val Val Asn Glu
 1               5                  10                  15 atc gct gcc aat att caa cga gag ata ctg aag gga gtg aaa agt tca      96
Ile Ala Ala Asn Ile Gln Arg Glu Ile Leu Lys Gly Val Lys Ser Ser
             20                  25                  30 gaa acc acc ctt acc atg ttc ctg aaa gag atg cag ctc aaa ggt ctt     144
Glu Thr Thr Leu Thr Met Phe Leu Lys Glu Met Gln Leu Lys Gly Leu
         35                  40                  45 cca aca tgt ggt gag act tgc ttt ggg gga act tgc aac act cct gga     192
Pro Thr Cys Gly Glu Thr Cys Phe Gly Gly Thr Cys Asn Thr Pro Gly
     50                  55                  60 tgc agt tgc tcc tcc tgg ccg att tgc act cgc aat ggc ctt cct aag     240
Cys Ser Cys Ser Ser Trp Pro Ile Cys Thr Arg Asn Gly Leu Pro Lys
 65                  70                  75                  80 agg gct gga gtg aaa agt tca gaa acc acc ctt acc atg ttc ctg aaa     288
Arg Ala Gly Val Lys Ser Ser Glu Thr Thr Leu Thr Met Phe Leu Lys
                 85                  90                  95 gag atg cag ctc aaa ggt ctt cca aca tgt ggt gag act tgc ttt ggg     336
Glu Met Gln Leu Lys Gly Leu Pro Thr Cys Gly Glu Thr Cys Phe Gly
            100                 105                 110 gga act tgc aac act cct gga tgc act tgc gat ccc tgg ccg att tgc     384
Gly Thr Cys Asn Thr Pro Gly Cys Thr Cys Asp Pro Trp Pro Ile Cys
        115                 120                 125 aca cgc gat ggc ctt cct agt gcg gcc gca                             414
Thr Arg Asp Gly Leu Pro Ser Ala Ala Ala
    130                 135
```

<210> SEQ ID NO 14
<211> LENGTH: 138
<212> TYPE: PRT
<213> ORGANISM: Oldenlandia affinis

<400> SEQUENCE: 14

```
Phe Gly Ala Glu Leu Ser Glu Ala Asp Lys Ala Asn Val Val Asn Glu
 1               5                  10                  15

Ile Ala Ala Asn Ile Gln Arg Glu Ile Leu Lys Gly Val Lys Ser Ser
             20                  25                  30

Glu Thr Thr Leu Thr Met Phe Leu Lys Glu Met Gln Leu Lys Gly Leu
         35                  40                  45

Pro Thr Cys Gly Glu Thr Cys Phe Gly Gly Thr Cys Asn Thr Pro Gly
     50                  55                  60

Cys Ser Cys Ser Ser Trp Pro Ile Cys Thr Arg Asn Gly Leu Pro Lys
 65                  70                  75                  80

Arg Ala Gly Val Lys Ser Ser Glu Thr Thr Leu Thr Met Phe Leu Lys
                 85                  90                  95

Glu Met Gln Leu Lys Gly Leu Pro Thr Cys Gly Glu Thr Cys Phe Gly
            100                 105                 110

Gly Thr Cys Asn Thr Pro Gly Cys Thr Cys Asp Pro Trp Pro Ile Cys
        115                 120                 125

Thr Arg Asp Gly Leu Pro Ser Ala Ala Ala
    130                 135
```

<210> SEQ ID NO 15
<211> LENGTH: 314
<212> TYPE: DNA
<213> ORGANISM: Oldenlandia affinis

<400> SEQUENCE: 15

```
taatttgctc gatcaaactg gaaaaatgaa taagaaggga caccaataaa gctatgaacg      60
ctgttggtcc cagtgtatct gttgatttgg ttggctccaa accatatgtg ctgcttgttt     120
tttttctttt tttcttttct ctttcgggca ctcttcatga catgaagaga tcatgatgac     180
tctttgttat tatgttttct gtgcacacct tccctgtac gtaggtgtgg ttcacatgtt      240
attgcccgaa tggaataaat tgtggttgtc gttgttatcg tactctctat tttaaattca     300
aaaaaaaaaa aaaa                                                        314
```

<210> SEQ ID NO 16
<211> LENGTH: 70
<212> TYPE: DNA
<213> ORGANISM: Oldenlandia affinis

<400> SEQUENCE: 16

```
aattcggcag gagcttctta taatttact gcttttctta tttctagaga aaggagaaat       60
tcgatcttcc                                                             70
```

<210> SEQ ID NO 17
<211> LENGTH: 60
<212> TYPE: DNA
<213> ORGANISM: Oldenlandia affinis
<220> FEATURE:
<221> NAME/KEY: CDS
<222> LOCATION: (1)...(60)

<400> SEQUENCE: 17

```
atg gct aag ttc acc aac tgt ctc gcc ctg tgc ttg ctt ctt gca gca       48
Met Ala Lys Phe Thr Asn Cys Leu Ala Leu Cys Leu Leu Leu Ala Ala
 1               5                  10                  15 gtt gtt ggg gct                                                        60
Val Val Gly Ala
            20
```

<210> SEQ ID NO 18
<211> LENGTH: 20
<212> TYPE: PRT
<213> ORGANISM: Oldenlandia affinis

<400> SEQUENCE: 18

```
Met Ala Lys Phe Thr Asn Cys Leu Ala Leu Cys Leu Leu Leu Ala Ala
 1               5                  10                  15

Val Val Gly Ala
            20
```

<210> SEQ ID NO 19
<211> LENGTH: 273
<212> TYPE: DNA
<213> ORGANISM: Oldenlandia affinis
<220> FEATURE:
<221> NAME/KEY: CDS
<222> LOCATION: (1)...(273)

<400> SEQUENCE: 19

```
ttc gga gtt gag ctt tct gaa gcc gac aag agc gcc gtg gtc aat gaa       48
```

```
Phe Gly Val Glu Leu Ser Glu Ala Asp Lys Ser Ala Val Val Asn Glu
 1               5                  10                  15 atc gct gag aag atg gcc cta cag gag atg ctg gac gga gtc gac aag     96
Ile Ala Glu Lys Met Ala Leu Gln Glu Met Leu Asp Gly Val Asp Lys
             20                  25                  30 ctg ttc ctg agg aag atg aaa agc tct gaa acc acc ctc acc atg ttc    144
Leu Phe Leu Arg Lys Met Lys Ser Ser Glu Thr Thr Leu Thr Met Phe
         35                  40                  45 ctg aaa gag atg cag ctc aaa ggt ctt cca gtc tgc ggt gag act tgc    192
Leu Lys Glu Met Gln Leu Lys Gly Leu Pro Val Cys Gly Glu Thr Cys
     50                  55                  60 act ttg gga act tgc tat act caa ggc tgc act tgc tcc tgg cct atc    240
Thr Leu Gly Thr Cys Tyr Thr Gln Gly Cys Thr Cys Ser Trp Pro Ile
 65                  70                  75                  80 tgc aag cgc aat ggc ctt cct gat gtg gcc gca                        273
Cys Lys Arg Asn Gly Leu Pro Asp Val Ala Ala
                 85                  90
```

<210> SEQ ID NO 20
<211> LENGTH: 91
<212> TYPE: PRT
<213> ORGANISM: Oldenlandia affinis

<400> SEQUENCE: 20

```
Phe Gly Val Glu Leu Ser Glu Ala Asp Lys Ser Ala Val Val Asn Glu
 1               5                  10                  15

Ile Ala Glu Lys Met Ala Leu Gln Glu Met Leu Asp Gly Val Asp Lys
             20                  25                  30

Leu Phe Leu Arg Lys Met Lys Ser Ser Glu Thr Thr Leu Thr Met Phe
         35                  40                  45

Leu Lys Glu Met Gln Leu Lys Gly Leu Pro Val Cys Gly Glu Thr Cys
     50                  55                  60

Thr Leu Gly Thr Cys Tyr Thr Gln Gly Cys Thr Cys Ser Trp Pro Ile
 65                  70                  75                  80

Cys Lys Arg Asn Gly Leu Pro Asp Val Ala Ala
                 85                  90
```

<210> SEQ ID NO 21
<211> LENGTH: 199
<212> TYPE: DNA
<213> ORGANISM: Oldenlandia affinis

<400> SEQUENCE: 21

```
taatttgctc gatcaaaaac tgcagaaatg aataagaagg gataccaaat aatgctatga     60
atattgttgg tccctgtgtc tgttgattgg gcactcttca tatgcataa agagatcttg    120 gatctgatat tggtcacatg ttaatacccca atttcaaaaa atcgttgtta tcgttgtcat   180
taaaaaaaaa aaaaaaaaa                                                 199
```

<210> SEQ ID NO 22
<211> LENGTH: 84
<212> TYPE: DNA
<213> ORGANISM: Oldenlandia affinis

<400> SEQUENCE: 22

```
aattcggcac cagatacaac ccctttctta taatttattg cttttcttat tccttgaaaa     60
aggagaaata atattggatc ttcc                                           84
```

<210> SEQ ID NO 23

```
<211> LENGTH: 60
<212> TYPE: DNA
<213> ORGANISM: Oldenlandia affinis
<220> FEATURE:
<221> NAME/KEY: CDS
<222> LOCATION: (1)...(60)

<400> SEQUENCE: 23 atg gct aag ttc acc aac tgt ctc gtc ctg agc ttg ctt cta gca gca    48
Met Ala Lys Phe Thr Asn Cys Leu Val Leu Ser Leu Leu Leu Ala Ala
 1               5                  10                  15 ttt gtt ggg gct                                                    60
Phe Val Gly Ala
            20

<210> SEQ ID NO 24
<211> LENGTH: 20
<212> TYPE: PRT
<213> ORGANISM: Oldenlandia affinis

<400> SEQUENCE: 24

Met Ala Lys Phe Thr Asn Cys Leu Val Leu Ser Leu Leu Leu Ala Ala
 1               5                  10                  15

Phe Val Gly Ala
            20

<210> SEQ ID NO 25
<211> LENGTH: 570
<212> TYPE: DNA
<213> ORGANISM: Oldenlandia affinis
<220> FEATURE:
<221> NAME/KEY: CDS
<222> LOCATION: (1)...(570)

<400> SEQUENCE: 25 ttc gga gct gag ttt tct gaa gcc gac aag gcc acc ttg gtc aat gat    48
Phe Gly Ala Glu Phe Ser Glu Ala Asp Lys Ala Thr Leu Val Asn Asp
 1               5                  10                  15 atc gct gag aat atc caa aaa gag ata ctg ggc gaa gtg aag act tct    96
Ile Ala Glu Asn Ile Gln Lys Glu Ile Leu Gly Glu Val Lys Thr Ser
                20                  25                  30 gaa acc gtc ctt acg atg ttc ctg aaa gag atg cag ctc aaa ggt ctt   144
Glu Thr Val Leu Thr Met Phe Leu Lys Glu Met Gln Leu Lys Gly Leu
        35                  40                  45 cca gta tgc ggc gag act tgc ttt ggg gga act tgc aac act cca ggc   192
Pro Val Cys Gly Glu Thr Cys Phe Gly Gly Thr Cys Asn Thr Pro Gly
 50                  55                  60 tgc tct tgc acc tgg cct atc tgc aca cgc gat agc ctt cct atg agg   240
Cys Ser Cys Thr Trp Pro Ile Cys Thr Arg Asp Ser Leu Pro Met Arg
 65                  70                  75                  80 gct gga gga aaa aca tct gaa acc acc ctt cat atg ttc ctg aaa gag   288
Ala Gly Gly Lys Thr Ser Glu Thr Thr Leu His Met Phe Leu Lys Glu
                85                  90                  95 atg cag ctc aag ggt ctt cca gtt tgc ggc gag act tgc ttt ggg gga   336
Met Gln Leu Lys Gly Leu Pro Val Cys Gly Glu Thr Cys Phe Gly Gly
            100                 105                 110 act tgc aac act cca ggc tgc tcg tgc acc tgg cct atc tgc aca cgc   384
Thr Cys Asn Thr Pro Gly Cys Ser Cys Thr Trp Pro Ile Cys Thr Arg
        115                 120                 125 gat agc ctt cct atg agt gct gga gga aaa aca tct gaa acc acc ctt   432
Asp Ser Leu Pro Met Ser Ala Gly Gly Lys Thr Ser Glu Thr Thr Leu
130                 135                 140 cat atg ttc ctg aaa gag atg cag ctc aag ggt ctt cca gtt tgc ggc   480
```

```
                His Met Phe Leu Lys Glu Met Gln Leu Lys Gly Leu Pro Val Cys Gly
                145                 150                 155                 160 gag act tgc ttt ggg gga act tgc aac act cca ggc tgc tcg tgc acc            528
Glu Thr Cys Phe Gly Gly Thr Cys Asn Thr Pro Gly Cys Ser Cys Thr
                165                 170                 175 tgg cct ata tgc aca cgt gat agc ctt cct ctt gtg gct gca                    570
Trp Pro Ile Cys Thr Arg Asp Ser Leu Pro Leu Val Ala Ala
                180                 185                 190
```

<210> SEQ ID NO 26
<211> LENGTH: 190
<212> TYPE: PRT
<213> ORGANISM: Oldenlandia affinis

<400> SEQUENCE: 26

```
Phe Gly Ala Glu Phe Ser Glu Ala Asp Lys Ala Thr Leu Val Asn Asp
1               5                   10                  15

Ile Ala Glu Asn Ile Gln Lys Glu Ile Leu Gly Glu Val Lys Thr Ser
                20                  25                  30

Glu Thr Val Leu Thr Met Phe Leu Lys Glu Met Gln Leu Lys Gly Leu
            35                  40                  45

Pro Val Cys Gly Glu Thr Cys Phe Gly Gly Thr Cys Asn Thr Pro Gly
        50                  55                  60

Cys Ser Cys Thr Trp Pro Ile Cys Thr Arg Asp Ser Leu Pro Met Arg
65                  70                  75                  80

Ala Gly Gly Lys Thr Ser Glu Thr Thr Leu His Met Phe Leu Lys Glu
                85                  90                  95

Met Gln Leu Lys Gly Leu Pro Val Cys Gly Glu Thr Cys Phe Gly Gly
            100                 105                 110

Thr Cys Asn Thr Pro Gly Cys Ser Cys Thr Trp Pro Ile Cys Thr Arg
        115                 120                 125

Asp Ser Leu Pro Met Ser Ala Gly Gly Lys Thr Ser Glu Thr Thr Leu
    130                 135                 140

His Met Phe Leu Lys Glu Met Gln Leu Lys Gly Leu Pro Val Cys Gly
145                 150                 155                 160

Glu Thr Cys Phe Gly Gly Thr Cys Asn Thr Pro Gly Cys Ser Cys Thr
                165                 170                 175

Trp Pro Ile Cys Thr Arg Asp Ser Leu Pro Leu Val Ala Ala
            180                 185                 190
```

<210> SEQ ID NO 27
<211> LENGTH: 284
<212> TYPE: DNA
<213> ORGANISM: Oldenlandia affinis
<220> FEATURE:
<221> NAME/KEY: misc_feature
<222> LOCATION: 229
<223> OTHER INFORMATION: n = A,T,C or G

<400> SEQUENCE: 27

```
taatttgctt catcaaactg caaaatgaat aagaagggac actaaattag ctatgaattt         60
tgttggccct tgtgtctggt aatttggttc ccgccaaatt aaccatatgt atgcattgct        120
ccttttttct ttctttttt tccccctcat ttgggcactc ttcattacat gaagagatca        180
tgacgctttg ttactctgag caccccctgt tggtgttgtt cacatgttna tgcccatgtt        240 ggaataaaact cttgttttg ttaccaaaaa aaaaaaaaa aaaa                          284
```

<210> SEQ ID NO 28

```
<211> LENGTH: 25
<212> TYPE: DNA
<213> ORGANISM: Artificial Sequence
<220> FEATURE:
<223> OTHER INFORMATION: Nucleotide sequence of Kal1 primer
<220> FEATURE:
<221> NAME/KEY: misc_feature
<222> LOCATION: 11, 14, 17, 23
<223> OTHER INFORMATION: n = A,T,C or G

<400> SEQUENCE: 28
cgggatccac nccnggntgy acntg                                           25

<210> SEQ ID NO 29
<211> LENGTH: 25
<212> TYPE: DNA
<213> ORGANISM: Artificial Sequence
<220> FEATURE:
<223> OTHER INFORMATION: Nucleotide sequence of Kal2 primer
<220> FEATURE:
<221> NAME/KEY: misc_feature
<222> LOCATION: 11, 17, 23
<223> OTHER INFORMATION: n = A,T,C or G

<400> SEQUENCE: 29
ggggatccgt ntgyggngar acntg                                           25

<210> SEQ ID NO 30
<211> LENGTH: 23
<212> TYPE: DNA
<213> ORGANISM: Artificial Sequence
<220> FEATURE:
<223> OTHER INFORMATION: Oligo-dT-HindIII nucleotide sequence

<400> SEQUENCE: 30
cgaagctttt ttttttttt ttt                                              23

<210> SEQ ID NO 31
<211> LENGTH: 90
<212> TYPE: DNA
<213> ORGANISM: Viola odorata
<220> FEATURE:
<221> NAME/KEY: CDS
<222> LOCATION: (1)...(90)

<400> SEQUENCE: 31 gtg tgt ggg gag acg tgc gtt ggt gga acc tgt aac acc cct ggg tgc     48
Val Cys Gly Glu Thr Cys Val Gly Gly Thr Cys Asn Thr Pro Gly Cys
 1               5                  10                  15 tct tgc agc tgg cct gtt tgc acc aga aac tct ctt gcc atg             90
Ser Cys Ser Trp Pro Val Cys Thr Arg Asn Ser Leu Ala Met
             20                  25                  30

<210> SEQ ID NO 32
<211> LENGTH: 30
<212> TYPE: PRT
<213> ORGANISM: Viola odorata

<400> SEQUENCE: 32

Val Cys Gly Glu Thr Cys Val Gly Gly Thr Cys Asn Thr Pro Gly Cys
 1               5                  10                  15

Ser Cys Ser Trp Pro Val Cys Thr Arg Asn Ser Leu Ala Met
             20                  25                  30

<210> SEQ ID NO 33
<211> LENGTH: 220
<212> TYPE: DNA
```

<210> SEQ ID NO 33
<211> LENGTH: 220
<212> TYPE: DNA
<213> ORGANISM: Viola odorata

<400> SEQUENCE: 33

```
taaggctgag atttaggcaa tgctcagatt tgttgtttct cgttctcgtt ctggttctgg      60
ttctcattat cgttattgtt cttgaggaga ggaggctata catgctcgtg acatgaaatt     120
agcaaaaagt aaaatgtcaa gcatgcctcc tcttcccttc ctttctgttt gaattaataa     180
aagtccagtt aattatttgt gctaaaaaaa aaaaaaaaa                            220
```

<210> SEQ ID NO 34
<211> LENGTH: 53
<212> TYPE: PRT
<213> ORGANISM: Oldenlandia affinis

<400> SEQUENCE: 34

Lys Thr Ser Glu Thr Ala Asp Gln Val Phe Lys Gln Leu Gln Leu
1               5                   10                  15

Lys Gly Leu Pro Val Cys Gly Glu Thr Cys Val Gly Gly Thr Cys Asn
            20                  25                  30

Thr Pro Gly Cys Thr Cys Ser Trp Pro Val Cys Thr Arg Asn Gly Leu
        35                  40                  45

Pro Ser Leu Ala Ala
        50

<210> SEQ ID NO 35
<211> LENGTH: 53
<212> TYPE: PRT
<213> ORGANISM: Oldenlandia affinis

<400> SEQUENCE: 35

Lys Thr Ser Glu Thr Val Leu Thr Met Phe Leu Lys Glu Met Gln Leu
1               5                   10                  15

Lys Gly Leu Pro Val Cys Gly Glu Thr Cys Phe Gly Gly Thr Cys Asn
            20                  25                  30

Thr Pro Gly Cys Ser Cys Thr Trp Pro Ile Cys Thr Arg Asp Ser Leu
        35                  40                  45

Pro Leu Val Ala Ala
        50

<210> SEQ ID NO 36
<211> LENGTH: 54
<212> TYPE: PRT
<213> ORGANISM: Oldenlandia affinis

<400> SEQUENCE: 36

Lys Ser Ser Glu Thr Thr Leu Thr Met Phe Leu Lys Glu Met Gln Leu
1               5                   10                  15

Lys Gly Leu Pro Thr Cys Gly Glu Thr Cys Phe Gly Gly Thr Cys Asn
            20                  25                  30

Thr Pro Gly Cys Thr Cys Asp Pro Trp Pro Ile Cys Thr Arg Asp Gly
        35                  40                  45

Leu Pro Ser Ala Ala Ala
        50

<210> SEQ ID NO 37
<211> LENGTH: 50
<212> TYPE: PRT
<213> ORGANISM: Oldenlandia affinis

<400> SEQUENCE: 37

-continued

```
Lys Ser Ser Glu Thr Thr Leu Thr Met Phe Leu Lys Glu Met Gln Leu
 1               5                  10                  15

Lys Gly Leu Pro Thr Cys Gly Glu Thr Cys Phe Gly Gly Thr Cys Asn
                20                  25                  30

Thr Pro Gly Cys Ser Cys Ser Ser Trp Pro Ile Cys Thr Arg Asn Gly
            35                  40                  45

Leu Pro
     50

<210> SEQ ID NO 38
<211> LENGTH: 53
<212> TYPE: PRT
<213> ORGANISM: Oldenlandia affinis

<400> SEQUENCE: 38

Lys Ser Ser Glu Thr Thr Leu Thr Met Phe Leu Lys Glu Met Gln Leu
 1               5                  10                  15

Lys Gly Leu Pro Val Cys Gly Glu Thr Cys Thr Leu Gly Thr Cys Tyr
                20                  25                  30

Thr Gln Gly Cys Thr Cys Ser Trp Pro Ile Cys Lys Arg Asn Gly Leu
            35                  40                  45

Pro Asp Val Ala Ala
     50

<210> SEQ ID NO 39
<211> LENGTH: 4
<212> TYPE: PRT
<213> ORGANISM: Oldenlandia affinis

<400> SEQUENCE: 39

Ser Ala Ala Ala
 1

<210> SEQ ID NO 40
<211> LENGTH: 4
<212> TYPE: PRT
<213> ORGANISM: Oldenlandia affinis

<400> SEQUENCE: 40

Ser Leu Ala Ala
 1
```

POLYNUCLEOTIDES ENCODING CYCLOTIDE-LIKE STRUCTURES

This application is a 371 of PCT/AU00/01352, filed Nov. 3, 2000, which claims the foreign priority of Australia PQ3884, filed Nov. 5, 1999, and Australia PQ4235, filed Nov. 25, 1999.

FIELD OF THE INVENTION

The present invention relates generally to a novel nucleic acid molecule encoding an amino acid sequence wherein said amino acid sequence or a derivative form thereof is capable of forming a cyclic structure. Cyclization may occur, for example, within a cell or cell membrane or linear forms of the molecules may be circularized or at least partly circularized in vitro using, for example, isolated enzyme systems or chemical means. The cyclised amino acid sequence is generally in the form of a stabilized folded structure such as a cyclic knotted peptide, polypeptide or protein or its functional equivalent. The present invention is further directed to cyclized molecules and in particular cyclic peptides, polypeptides or proteins, linear forms thereof including non-cyclic structural homologues of the cyclic peptides, polypeptides and proteins and precursor or derivative forms thereof encoded by the subject nucleic acid molecules. The nucleic acid molecules and cyclic and linear peptides, polypeptides and proteins of the present invention are useful inter alia in the generation of molecules having animal or plant therapeutic properties as well as in a range of diagnostic, industrial and agricultural including horticultural applications. Of particular importance is the use of these molecules in the protection of plants such as crop plants from pest and/or pathogen infestation. The cyclic and linear peptides, polypeptides and polypeptides may be naturally occurring or may be modified by the insertion or substitution of heterologous amino acid sequences. The therapeutic properties may be inherent in the naturally occurring cyclic or linear molecules and/or may be associated with the heterologous amino acid sequence. The present invention further provides microbial, plant and animal cell systems as well as in vitro systems capable of cyclizing linear forms of the peptides, polypeptides and proteins of the present invention. The present invention also extends to the peptide, polypeptide or protein sequences which are capable of cyclizing in the absence of any other exogenous factor and more specifically capable of circularizing through a catalytic process being an inherent activity of the peptides, polypeptides or proteins.

BACKGROUND OF THE INVENTION

Bibliographic details of the publications numerically referred to in this specification are collected at the end of the description.

Reference to any prior art in this specification is not, and should not be taken as, an acknowledgment or any form of suggestion that this prior art forms part of the common general knowledge in Australia or any other country.

A number of macrocyclic peptides with diverse biological activities have been discovered in plants in the Rubiaceae and Violaceae families. These include kalata B1 (1), the circulins (2), cyclopsychotride (3) and several peptides from Viola species (4-6). They range in size from 29-31 amino acids and contain six conserved Cys residues. These macrocyclic peptides differ from classical proteins in that they have no free N- or C-terminus due to their amide-circularized backbone. They also incorporate a cystine knot in which an embedded ring in the structure formed by two disulfide bonds and their connecting backbone segments is threaded by a third disulfide bond. These combined features of the cyclic cystine knot (CCK) produce a unique protein fold that is topologically complex and has exceptional chemical and biological stability.

Small cyclic peptides are also known in nature, particularly as antibiotics of microbial origin, and appear to have advantages of improved stability and biological activity over their non-cyclic counterparts. Because of their favourable properties, cyclic peptides (or mimics of them) have had pharmaceutical applications. One example is the immunosuppressent, cyclosporine. These classical cyclic peptides invariably comprise fewer than 15 amino acids, usually lack disulfide bonds and generally do not have well defined three dimensional structures. Such peptides are not gene products but are thought to be biosynthesized, non-ribosomally, via peptide synthetases.

In work leading up to the present invention, the inventors investigated the genetic basis of the macrocyclic peptides. In contrast to small cyclic peptides, the macrocyclic peptides, referred to herein as "cyclotides", are encoded for by gene sequences and exhibit folding structures characteristic of true proteins. The elucidation of the genetic basis behind the cyclotides enables their expression and manipulation in transgenic plant, animal and microbial cells. Being cyclic, the cyclotides have a range of potential therapeutic, diagnostic, industrial and agricultural including horticultural applications. The cyclizing enzyme or enzymes themselves also have utility in the development of in vivo or in vitro systems for cyclizing target peptides, polypeptides and proteins. Furthermore, the present invention permits the generation of linear structural homologues of peptides, polypeptides and proteins.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier, i.e. SEQ ID NO: 1, SEQ ID NO: 2, etc. A sequence listing is provided after the claims.

One aspect of the present invention provides an isolated nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell to form a cyclic backbone wherein said cyclic backbone comprises sufficient disulfide bonds to confer a stabilized folded structure on the three dimensional structure of said backbone.

Another aspect of the present invention present is directed to an isolated nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell to form a cyclic knotted peptide, polypeptide or protein.

A further aspect of the present invention provides a nucleic acid molecule comprising a sequence of nucleotides which encodes or is complementary to a sequence which encodes an amino acid sequence capable of forming a cyclic backbone wherein the cyclic backbone comprises the structure:

wherein
  C is cysteine;
  each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
  wherein a, b, c, d, e and f represent the number of amino acid residues in each respective sequence and each of a to f may be the same or different and range from 1 to about 20.

Still another aspect of the present invention provides a nucleic acid molecule comprising a sequence of nucleotides which encodes or is complementary to a sequence which encodes an amino acid sequence capable of forming a cyclic backbone wherein the cyclic backbone comprises the structure:

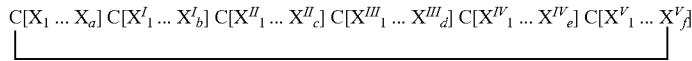

wherein
  C is cysteine;
  each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
  wherein a, b, c, d, e and f represent the number of amino acid residues in each respective sequence and each of a to f may be the same or different and range from 1 to about 10.

Even still another aspect of the present invention provides a nucleic acid molecule comprising a sequence of nucleotides which encodes or is complementary to a sequence which encodes an amino acid sequence capable of forming a cyclic backbone wherein the cyclic backbone comprises the structure:

wherein
  C is cysteine;
  each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
  wherein a, b, c, d, e and f represent the number of amino acid residues in each respective sequence and wherein a is from about 3 to about 6, b is from about 3 to about 5, c is from about 2 to about 7, d is about 1 to about 3, e is about 3 to about 6 and f is from about 4 to about 9.

Yet another aspect of the present invention provides a nucleic acid molecule an isolated nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell in an in vitro cyclizing system to form a cyclic backbone wherein the cyclic backbone comprises the structure:

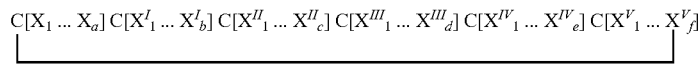

wherein
  C is cysteine;
  each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
  wherein a, b, c, d, e and f represent the number of amino acid residues in each respective sequence and each of a is about 3, b is about 4, c is about from 4 to about 7, d is about 1, e is about 4 or 5 and f is from about 4 to about 7.

Even yet another aspect of the present invention provides a nucleic acid molecule an isolated nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell in an in vitro cyclizing system to form a cyclic backbone wherein the cyclic backbone comprises the structure:

wherein

C is cysteine;

each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and wherein a, b, c, d, e and f represent the number of amino acid residues in each respective sequence and wherein a is about 6, b is about 5, c is about 3, d is about 1, e is about 5 and f is about 8.

A further aspect of the present invention provides an isolated nucleic acid molecule comprising a sequence of nucleotides, which sequence of nucleotides, or its complementary form, encodes an amino acid sequence wherein the amino acid sequence or a derivative form thereof is capable of forming a structural homologue of a cyclic peptide, polypeptide or protein within a cell or a membrane of a cell to form a backbone wherein said backbone comprises sufficient disulfide bonds to confer a stabilized folded structure on the three-dimensional structure of said backbone wherein said backbone comprises free amino and carboxy termini.

Another aspect of the present invention contemplates a method of identifying nucleic acid molecules which encode one or more enzymes required for cyclization of an amino acid sequence said method comprising obtaining a nucleic acid molecule which encodes a precursor form of an amino acid sequence capable of being cyclized into a knotted peptide, polypeptide or protein; introducing or fusing to said nucleic acid molecule, a nucleotide sequence which encodes a reporter molecule capable of providing a detectable signal wherein said nucleotide sequence is inserted or fused to a portion of the nucleic acid molecule which is cleaved off prior to or during cyclization; introducing said nucleic acid molecule comprising the nucleotide sequence encoding the reporter molecule into a bank of cells carrying a DNA library comprising all or part of genomic DNA or cDNA from a plant which carries the enzyme or enzymes required for cyclization of an amino acid sequence; screening for and selecting cells which do not synthesize the reporter molecule.

A further aspect of the present invention contemplates a genetically modified cell or cells or a plant or animal comprising said genetically modified cells, said cells comprising a nucleic acid molecule having a nucleotide sequence or complementary nucleotide sequence which encodes an amino acid sequence capable of being cyclized into a knotted peptide, polypeptide or protein.

Still another aspect of the present invention contemplates a method of incorporating an amino acid sequence conferring a particular trait into a cyclic peptide, polypeptide or protein, said method comprising fusing or introducing a nucleotide sequence encoding said amino acid sequence to or into a second nucleotide sequence wherein said second nucleotide sequence encodes a peptide, polypeptide or protein which peptide, polypeptide or protein or a derivative therefor is capable of being cyclized into a knotted peptide, polypeptide or protein.

Even still another aspect of the invention contemplates an isolated nucleic acid molecule comprising the following nucleotide sequence:

$$[X_1 \ldots X_b[n_1 n_2 \ldots n_a]y_1 \ldots y_c]_d$$

wherein $[n_1 n_2 \ldots n_a]$ represents a nucleotide sequence encoding an amino acid sequence capable of being cyclized to a knotted peptide or polypeptide or protein; and $X_1 \ldots X_b$ and $y_1 \ldots y_c$ represent polynucleotide sequences capable of encoding an amino acid sequence where a and b and c and d may be any number and when d is >1, the amino acid sequence may be unique for each integer of d.

Yet another aspect of the invention contemplates an isolated nucleic acid molecule comprising the following nucleotide sequence:

$$j_1 \ldots j_e[X_1 \ldots X_a[n_1 n_2 \ldots n_a]y_1 \ldots y_c]_d q_1 \ldots q_f$$

wherein $[n_1 n_2 \ldots n_a]$ represents a nucleotide sequence encoding an amino acid sequence capable of being cyclized to a knotted peptide or polypeptide or protein;

$X_1 \ldots X_b$ and $y_1 \ldots y_c$ represent polynucleotide sequences capable of encoding an amino acid sequence where a and b and c and d may be any number and when d is >1, the amino acid sequence may be unique for each integer of d; and $j_1 \ldots j_e$ and $q_1 \ldots q_f$ represent nucleotide sequences encoding a peptide, polypeptide or protein capable of directing the peptide, polypeptide or protein to a cellular compartment or organelle where a, b, c, d, e and f may be any number, where d is >1, the amino acid sequence may be unique for each integer of d.

Even yet another aspect of the invention contemplates an isolated nucleic acid molecule comprising the following nucleotide sequence:

$$[X_1 \ldots X_b[n_1 n_2 \ldots (k_1 \ldots k_\delta)_\lambda n_a]y_1 \ldots y_c]_d$$

wherein $[n_1 n_2 \ldots n_a]$ represents a nucleotide sequence encoding an amino acid sequence capable of being cyclized to a knotted peptide or polypeptide or protein;

$X_1 \ldots X_b$ and $y_1 \ldots y_c$ represent polynucleotide sequences capable of encoding an amino acid sequence where a and b and c and d, δ and λ may be any number and when d or λ is >1, the amino acid sequence may be unique for each integer of d and λ;

$k_1 \ldots k_\delta$ represent a nucleotide sequence encoding an amino acid sequence conferring a particular activity or other trait.

Another aspect of the invention contemplates an isolated nucleic acid molecule comprising the following nucleotide sequence:

$$[n_1 n_2 \ldots (n_1 n_2 \ldots (n_1^I n_2^I \ldots n_\gamma^I) \ldots n_a]_m$$

wherein $[n_1 n_2 \ldots n_a]$ and $(n_1^I n_2^I \ldots n_\gamma^I)$ represent polynucleotide sequences encoding an amino acid sequence capable of being cyclized to a knotted peptide or polypeptide or protein; and γ and a and m may be any number and when m is >1, the amino acid sequence may be unique for each integer of m.

A further aspect of the invention contemplates an isolated nucleic acid molecule comprising the following nucleotide sequence:

$$j_1 \ldots j_e[X_1 \ldots X_b[n_1 n_2 \ldots (n_1^I n_2^I \ldots (k_1 \ldots k_\delta)_\lambda n_a)_m n_a]y_1 \ldots y_c]_d q_1 \ldots q_f$$

wherein $[n_1 n_2 \ldots n_a]$ represents a nucleotide sequence encoding an amino acid sequence capable of being cyclized to a knotted peptide or polypeptide or protein;

$X_1 \ldots X_b$ and $y_1 \ldots y_c$ represents a polynucleotide sequence capable of encoding an amino acid sequence where a and b and c and d and e may be any number and when d is >1, the amino acid sequence may be unique for each integer of d;

$j_1 \ldots j_e$ and $q_1 \ldots q_f$ represents a nucleotide sequence encoding a peptide, polypeptide or protein capable of directing the peptide, polypeptide or protein to a cellular compartment or organelle;

$k_1 \ldots k_\delta$ represents a nucleotide sequence encoding an amino acid sequence conferring a particular activity or other trait;

$\lambda$ and m and d may be any number and when $\lambda$ and m and d are each >1, the amino acid sequence may be unique for each integer of $\lambda$, m and d.

Yet another aspect of the present invention further contemplates a genetically modified plant which comprises a nucleotide sequence which encodes an amino acid sequence capable of being cyclized into a knotted peptide, polypeptide or protein and which confers on said plant a trait not present in the same species or variety of plant prior to genetic modification.

Even yet another aspect of the present invention provides the use of a nucleic acid molecule encoding an amino acid sequence, which amino acid sequence or a derivative or precursor form thereof is capable of being cyclized into a knotted peptide, polypeptide or protein, in the manufacture of a transgenic or genetically modified plant capable of producing said cyclic knotted peptide, polypeptide or protein.

Still yet another aspect of the present invention relates to an immunointeractive molecule specific for a peptide, polypeptide or protein when in cyclic form and encoded by a nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell to form a cyclic backbone wherein said cyclic backbone comprises sufficient disulfide bonds to confer a stabilized folded structure on the three dimensional structure of said backbone.

Another aspect of the present invention is directed to an immunointeractive molecule specific for a peptide, polypeptide or protein encoded by a nucleic acid molecule comprising a sequence of nucleotides, which sequence of nucleotides, or its complementary form, encodes an amino acid sequence wherein the amino acid sequence or a derivative form thereof is capable of forming a structural homologue of a cyclic peptide, polypeptide or protein within a cell or a membrane of a cell to form a backbone wherein said backbone comprises sufficient disulfide bonds to confer a stabilized folded structure on the three dimensional structure of said backbone wherein said backbone comprises free amino and carboxy termini.

BRIEF DESCRIPTION OF THE FIGURES

FIG. 2 is a presentation of the sequence of the 412 bp DNA fragment amplified from *O. affinis* cDNA with primers complementary to the Kalata B1 sequence (FIG. 1C, fragment 5). The 412 bp fragment has an open reading frame SEQ ID NO: 7 that encodes the entire 29 amino acids of Kalata B1 SEQ ID NO: 8 together with an additional four amino acids at the C-terminus. The 3' untranslated region is shown in SEQ ID NO: 9. The primer sequences are shown in italics, stop codons are indicated by "*" and a region corresponding to the sequence of the mature peptide is underlined.

FIG. 3 is a photographic representation showing gel bot analysis of RNA from *O. affinis* leaves. (A) The RNA blot. The Kalata B1 cDNA (see FIG. 2) hybridized to a single RNA transcript of ~750 bases. (B) Identical gel to (A) stained with ethidium bromide to reveal the rRNA bands. Size markers were the 0.28-6.58 kb RNA markers from Promega.

FIG. 4 is a representation of nucleotide sequence SEQ ID NO: 4 and predicted amino-acid sequence SEQ ID NO: 5 of Oak1, the cDNA encoding Kalata B1 from *O. affinis*. The 5' and 3' ends of the DNA are shown in SEQ ID NO: 1 and SEQ ID NO: 6, respectively. The nucleotide sequence encoding the signal peptide and the corresponding amino acid sequence is shown in SEQ ID NO: 3 or SEQ ID NO: 4, respectively. Only one strand with the polarity of the mRNA is shown. Nucleotides are numbered above the sequence. The amino acid sequence, shown in single letter code is numbered beginning with 1 for the predicted first amino acid in the precursor protein. The putative signal peptide is indicated by negative numbers. An amino acid sequence subjected to processing to give Kalata B1 is shaded. Arrows indicate potential processing sites. The underlined region at the N-terminus of the Kalata B1 domain (NT-conserved) is highly conserved in other Oak clones (see FIGS. 8A and 8B).

FIG. 5 is a representation of the nucleotide sequence (SEQ ID NO: 13) and predicted amino-acid sequence (SEQ ID NO: 14) of Oak2, the cDNA encoding Kalata B3 and B6 from *O. affinis*. Only one strand with the polarity of the mRNA is shown. Nucleotides are numbered above the sequence. The amino acid sequence, shown in single letter code, is numbered beginning with 1 for the predicted first amino acid in the precursor protein. The putative signal peptide is indicated by negative numbers SEQ ID NO: 12 and is encoded by the nucleotide sequence set forth in SEQ ID NO: 11. An amino acid sequence subjected to processing to give Kalata B3 and B6 is shaded. Dark and light shading respectively highlights the sequence of Kalata B3 and B6. Arrows indicate potential processing sites. The underlined region at the N-terminus of the Kalata B3 and B6 domains (NT-conserved) is highly conserved in other Oak clones (see FIGS. 8A and 8B). The untranslated 5' and 3' ends of the DNA is shown in SEQ ID NO: 10 and SEQ ID NO: 15, respectively.

FIG. 6 is a representation of the nucleotide sequence (SEQ ID NO: 19) and predicted amino-acid sequence (SEQ ID NO: 20) of Oak3, the cDNA encoding Kalata B7 from *O. affinis*. Only one strand with the polarity of the mRNA is shown. Nucleotides are numbered above the sequence. The amino acid sequence, shown in single letter code, is numbered beginning with 1 for the first predicted amino acid in the precursor protein. The putative signal peptide (SEQ ID NO: 18) is indicated by negative numbers and is encoded by the nucleotide sequence set forth in SEQ ID NO: 17. An amino acid sequence subjected to processing to give Kalata B7 is shaded. Arrows indicate potential processing sites. The underlined region at the N-terminus of the Kalata B7 domain (NT-conserved) is highly conserved in other Oak clones (see FIGS. 8A and 8B). The untranslated 5' and 3' ends of the DNA is shown in SEQ ID NO: 16 and SEQ ID NO: 21, respectively.

FIG. 7 is a representation of the nucleotide sequence SEQ ID NO: 25 and predicted amino acid sequence SEQ ID NO: 26 of Oak4, the cDNA encoding Kalata B2 from *O. affinis*. Only one strand with the polarity of the mRNA is shown. Nucleotides are numbered above the sequence. The amino acid sequence, shown in single letter code, is numbered beginning with 1 for the first predicted amino acid in the precursor protein. The putative signal peptide SEQ ID NO: 24 is indicated by negative numbers and is encoded by SEQ ID NO: 23. An amino acid sequence subjected to processing to give Kalata B2 (shaded) is repeated three times. Arrows indicate potential processing sites. The underlined region at the N-terminus of the Kalata 132 domain (NT-conserved) is highly conserved in other Oak clones (see, FIGS. 8A and 8B). The untranslated 5' and 3' ends of the DNA is shown in SEQ ID NO: 22 and SEQ ID NO: 27, respectively.

FIG. 8 is a schematic diagram of (A) of the precursor proteins predicted from the Oak1, 2, 3 and 4 clones showing the signal peptide, the regions corresponding to the mature kalata peptides (shaded), the region of 17 conserved amino acids on the N-terminal side of the kalata peptide sequence (N-T conserved, hatched), and (B) the sequence around the potential processing sites. The mature cyclic peptide retains one copy of the Gly-Leu-Pro sequence, which may be derived entirely from one of the two flanking elements (shaded), or partially from both depending on the initial cleavage sites.

FIG. 15 is a representation of the sequence of the 311 by fragment amplified from *Viola odorata* cDNA with the primers Kal2 and oligo dT-HindIII (see FIG. 1). The 311 bp fragment has an open reading frame SEQ ID NO: 31 that encodes 26 amino acids SEQ ID NO: 32 of Kalata S (underlined) a cyclotide isolated from *V. odorata* (12). An additional four amino acids are located at the C-terminus of the Kalata S sequence. The primer sequences are shown in italics, the stop codon is indicated by "*" and the coding region is underlined. The untranslated 3' end of the DNA is shown in SEQ ID NO: 33.

Figures 1A, 1B:
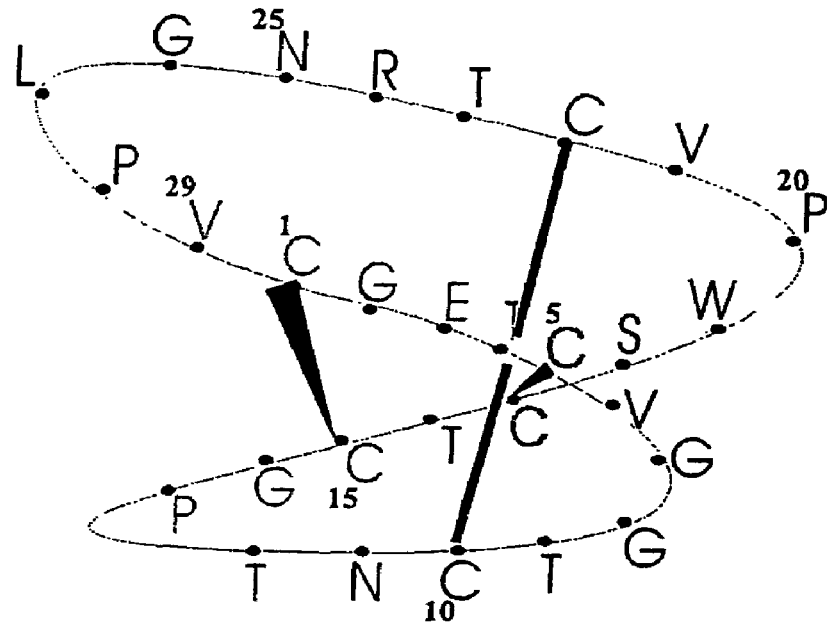
FIG. 1 is a representation showing (A) the amino acid sequence of Kalata B1. The Kalata B1 peptide is composed of 29 amino acids and has a cyclic peptide backbone; (B) the primers used in the PCR reactions. Primers Kal1 SEQ ID NO: 28 and Kal2 SEQ ID NO: 29 correspond to amino acid residues 12 to 17 or 29 to 5 (see FIG. 1A). I represents inosine, Y represents C or T, and R represents A, C, T or G. The encoded amino acids are represented in single letter code and the introduced restriction enzyme sites are in italics; and (C) the PCR products. cDNA prepared from *O. affinis* leaf RNA was amplified with primers Kal1 and oligo dT-HindIII (lane 1) or primers Kal2 and oligo-dT-HindIII (lane 2) SEQ ID NO: 31. The amplified fragments were separated on a 2% w/v agarose gel and stained with ethidium bromide. Five major fragments were obtained, two from primer Kal1 (1-2) and three from primer Kal2 (3-5). Fragments 1 and 5 were subcloned and sequenced.

Table 1 is a summary of single and three letter abbreviations used throughout the specification are defined in Table 1.

Table 2 is a summary of amino acid and nucleotide sequence identifiers.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |

TABLE 1-continued

Single and three letter amino acid abbreviations

| Amino Acid | Three-letter Abbreviation | One-letter Symbol |
|---|---|---|
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |
| Valine | Val | V |
| Any residue | Xaa | X |

TABLE 2

| SEQUENCE IDENTIFIER | DESCRIPTION |
|---|---|
| SEQ ID NO:1 | Untranslated 5' end of DNA encoding Kalata B1 |
| SEQ ID NO:2 | Nucleotide sequence encoding signal peptide of Kalata B1 |
| SEQ ID NO:3 | Amino acid sequence of signal peptide of Kalata B1 |
| SEQ ID NO:4 | Nucleotide sequence of cDNA encoding Kalata B1 |
| SEQ ID NO:5 | Amino acid sequence of Kalata B1 encoded by SEQ ID NO:4 |
| SEQ ID NO:6 | Untranslated 3' end of DNA encoding Kalata B1 |
| SEQ ID NO:7 | Partial nucleotide sequence of a 400 by DNA fragment amplified from *O. affins* cDNA |
| SEQ ID NO:8 | Partial amino acid sequence encoded by SEQ ID NO:7 |
| SEQ ID NO:9 | Untranslated 3' end of 400 bp DNA fragment from *O. affins* cDNA |
| SEQ ID NO:10 | Untranslated 5' end of DNA encoding Kalata B3 and B6 |
| SEQ ID NO:11 | Nucleotide sequence encoding signal peptide of Kalata B3 and B6 |
| SEQ ID NO:12 | Amino acid sequence of signal peptide of Kalata B3 and B6 |
| SEQ ID NO:13 | Nucleotide sequence of cDNA encoding Kalata B3 and B6 |
| SEQ ID NO:14 | Amino acid sequence of Kalata B3 and B6 |
| SEQ ID NO:15 | Untranslated 3' end of DNA encoding Kalata B3 and B6 |
| SEQ ID NO:16 | Untranslated 5' end of DNA encoding Kalata B7 |
| SEQ ID NO:17 | Nucleotide sequence encoding signal peptide of Kalata B7 |
| SEQ ID NO:18 | Amino acid sequence of signal peptide of Kalata B7 |
| SEQ ID NO:19 | Nucleotide sequence of cDNA encoding Kalata B7 |
| SEQ ID NO:20 | Amino acid sequence of Kalata B7 |
| SEQ ID NO:21 | Untranslated 3' end of DNA encoding Kalata B7 |
| SEQ ID NO:22 | Untranslated 5' end of DNA encoding Kalata B2 |
| SEQ ID NO:23 | Nucleotide sequence encoding signal peptide of Kalata B2 |
| SEQ ID NO:24 | Amino acid sequence of signal peptide of Kalata B2 |
| SEQ ID NO:25 | Nucleotide sequence of cDNA encoding Kalata B2 |
| SEQ ID NO:26 | Amino acid sequence of Kalata B2 |
| SEQ ID NO:27 | Untranslated 3' end of DNA encoding Kalata B2 |
| SEQ ID NO:28 | Nucleotide sequence of Kal1 primer |
| SEQ ID NO:29 | Nucleotide sequence of Kal2 primer |
| SEQ ID NO:30 | Oligo-dT-HindIII nucleotide sequence |
| SEQ ID NO:31 | Nucleotide sequence of coding region of 311 by fragment amplified by *Viola odorata* cDNA |
| SEQ ID NO:32 | Amino acid sequence encoded by SEQ ID NO:31 |
| SEQ ID NO:33 | Untranslated 3' end of 311 by fragment amplified from *Viola odorata* cDNA |

DETAILED DESCRIPTION OF THE PREFERRED EMBODIMENTS

The present invention is predicated in part on the elucidation of the genetic basis behind the production of macrocyclic peptides.

Accordingly, one aspect of the present invention provides an isolated nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell to form a cyclic backbone wherein said cyclic backbone comprises sufficient disulfide bonds to confer a stabilized folded structure on the three dimensional structure of said backbone.

The term "knotted" is not to be limited by any mathematical or geometrical definition of the term "knot". The knots contemplated by the present invention are such due to their similarity to a mathematical knot and/or by virtue of the intertwined folding of the molecule which results.

Preferably, the stabilized folded structure contains a knotted topology. Accordingly, the present invention is directed, therefore, to an isolated nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell to form a cyclic knotted peptide, polypeptide or protein. The amino acid sequence may also be cyclizable in an in vitro system comprising, for example, cyclizing enzymes or the chemical means for cyclization.

An "isolated nucleic acid molecule" is a nucleic acid molecule which has undergone at least one purification step from a biological sample. Purification steps include inter alia precipitation, centrifugation, chromatography, electrophoresis and/or filtration. The nucleic acid molecule may be single or double stranded RNA or DNA or an RNA:DNA hybrid.

The nucleic acid molecule may comprise naturally occurring nucleotide bases or the bases may be synthetic or chemical analogues of bases or be chemically modified such as a C-5 propyne or phosphorothiolate modification.

An "amino acid sequence" generally means a sequence of two or more amino acid residues. In terms of the cyclotides of the present invention, generally the amino acid sequence comprises at least from about 100 to about 150 amino acid residues, preferably from about 15 to about 100 amino acid residues and even more preferably from about 15 to about 50 amino acid residues, when in cyclic form. The amino acid sequence referred to herein may be considered a peptide or polypeptide and these terms are used interchangedly in the subject specification. A "polypeptide" may also be considered a "protein".

However, the nucleic acid molecule of the present invention may first encode a precursor, peptide, polypeptide or protein, generally in linear form. Such a precursor may comprise from about 50 to about 1000 amino acid residues or from about 50 to about 500 amino acid residues or from about 50 to about 300 amino acid residues.

The precursor amino acid sequence is derivatized to a smaller amino acid sequence which is then cyclized. Alternatively, the cyclization process may include a derivatization step. The cyclization step may also occur in vitro using isolated enzyme systems or using chemical means.

Reference to a "derivative" of the amino acid sequence includes the derivatization of a precursor sequence to a cyclizable sequence.

The present invention extends to the nucleic acid molecule encoding the cyclotide or its linear precursor. Furthermore, the "cyclotide" may be linear in the sense that it has free amino acid and carboxy termini but still folds into a knot arrangement. Such a linear form is regarded as a structural homologue of the cyclotide.

Accordingly, another aspect of the present invention contemplates an isolated nucleic acid molecule comprising a sequence of nucleotides, which sequence of nucleotides, or its complementary form, encodes an amino acid sequence wherein the amino acid sequence or a derivative form thereof is capable of forming a structural homologue of a cyclic peptide, polypeptide or protein within a cell or a membrane of a cell to form a backbone wherein said backbone comprises sufficient disulfide bonds to confer a stabilized folded structure on the three dimensional structure of said backbone wherein said backbone comprises free amino and carboxyl termini.

Reference herein to a "cyclic backbone" preferably includes a molecule comprising a sequence of amino acid residues or homologues thereof without free amino acid and carboxy and amino termini.

The cyclic backbone encoded by the nucleic acid molecule of the present invention comprises sufficient disulfide bonds, or chemical equivalents thereof, to confer a stabilized folded structure on the three dimensional structure of the cyclic backbone.

Preferably, the stabilized folded structure comprises a knotted topology.

In a preferred embodiment, the cyclic backbone comprises a cystine knot. A cystine knot occurs when a disulfide bond passes through a closed cyclic loop formed by two other disulfide bonds and the amino acids in the backbone. Such a cystine knot is referred to herein as "cyclic cystine knot" or "CCK". Reference herein, however, to a cyclic cystine knot or a CCK includes reference to structural equivalents thereof which provide similar constraints to the three dimensional structure of the cyclic backbone. For example, appropriate turns and loops in the cyclic backbone may also be achieved by engineering suitable covalent bonds or other forms of molecular associations. All such modifications to the cyclic backbone which retains the three-dimensional knotted topology conferred by the cyclic cystine knot are encompassed by the present invention including such modifications to the nucleic acid molecule which encodes a modified cyclotide. Furthermore, although a cyclic cystine knot is characterized by a knot formed on three disulfide bonds, the present invention extends to molecules comprising only two disulfide bonds. In such a case, the cyclic peptide, polypeptide or protein may need to be further stabilized using other means or the molecule may retain suitable activity despite a change in three-dimensional structure caused by the absence of a third disulfide bond. Reference herein to a "knotted topology" is not to be construed as limiting the invention to such a topology alone since the instant invention extends to any stabilizing folded structure. Furthermore, the cyclic backbone may comprise more than three disulfide bonds such as occurring in a double or multiple cystine knot arrangement or in a single cystine knot arrangement supplemented by one or two additional disulfide bonds.

Another aspect of the present invention provides a nucleic acid molecule comprising a sequence of nucleotides which encodes or is complementary to a sequence which encodes an amino acid sequence capable of forming a cyclic backbone wherein the cyclic backbone comprises the structure:

$$C[X_1 \ldots X_a] \ C[X^I_1 \ldots X^I_b] \ C[X^{II}_1 \ldots X^{II}_c] \ C[X^{III}_1 \ldots X^{III}_d] \ C[X^{IV}_1 \ldots X^{IV}_e] \ C[X^V_1 \ldots X^V_f]$$

wherein
  C is cysteine;
  each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
  wherein a, b, c, d, e and f represent the number of amino acid residues in each respective sequence and each of a to f may be the same or different and range from 1 to about 20.

Preferably, each of a to f ranges from 1 to about 10.

In a particularly preferred embodiment, the present invention provides a nucleic acid molecule comprising a sequence of nucleotides which encodes or is complementary to a sequence which encodes an amino acid sequence capable of forming a cyclic backbone wherein the cyclic backbone comprises the structure:

$$C[X_1 \ldots X_a] \ C[X^I_1 \ldots X^I_b] \ C[X^{II}_1 \ldots X^{II}_c] \ C[X^{III}_1 \ldots X^{III}_d] \ C[X^{IV}_1 \ldots X^{IV}_e] \ C[X^V_1 \ldots X^V_f]$$

wherein
  C is cysteine;
  each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
  wherein a, b, c, d, e and f represent the number of amino acid residues in each respective sequence and wherein a is from about 3 to about 6, b is from about 3 to about 5, c is from about 2 to about 7, d is about 1 to about 3, e is about 3 to about 6 and f is from about 4 to about 9.

In an even more particularly preferred embodiment, the present invention provides a nucleic acid molecule an isolated nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell in an in vitro cyclizing system to form a cyclic backbone wherein the cyclic backbone comprises the structure:

$$C[X_1 ... X_a] \, C[X^I_1 ... X^I_b] \, C[X^{II}_1 ... X^{II}_c] \, C[X^{III}_1 ... X^{III}_d] \, C[X^{IV}_1 ... X^{IV}_e] \, C[X^V_1 ... X^V_f]$$

wherein
C is cysteine;
each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
wherein a, b, c, d, e and f represent the number of amino acid residues in each respective sequence and each of a is about 3, b is about 4, c is about from 4 to about 7, d is about 1, e is about 4 or 5 and f is from about 4 to about 7.

In still an even more particularly preferred embodiment, the present invention provides a nucleic acid molecule an isolated nucleic acid molecule comprising a sequence of nucleotides, which sequence of nucleotides, or its complementary form, encodes an amino acid sequence wherein the amino acid sequence or a derivative form thereof is capable of being cyclized within a cell or a membrane of a cell in an in vitro cyclizing system to form a cyclic backbone wherein the cyclic backbone comprises the structure:

$$C[X_1 ... X_a] \, C[X^I_1 ... X^I_b] \, C[X^{II}_1 ... X^{II}_c] \, C[X^{III}_1 ... X^{III}_d] \, C[X^{IV}_1 ... X^{IV}_e] \, C[X^V_1 ... X^V_f]$$

wherein
C is cysteine;
each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
wherein a, b, c, d, e and f represent the number of amino acid residues in each respective sequence and wherein a is about 6, b is about 5, c is about 3, d is about 1, e is about 5 and f is about 8.

The invention extends to and includes peptide, polypeptide and protein sequences which have not been acted upon by an enzyme system separate from the molecule itself. For example, the present invention extends to autocatalytic cyclization.

The cyclization of the amino acid sequence may occur in a cell such as a plant cell or cell membrane which naturally contains the cyclization enzyme or enzymes. An in vitro system may also be employed with isolated enzyme(s) capable of cyclizing target molecules. Chemical means may also be employed to facilitate cyclization. Alternatively, cells may be engineered to express the genes encoding the cyclization enzyme or enzymes. In relation to the former, preferred cells are whole plants, callus or cell lines or membranous preparations of cells from the Rubiaceae, Violaceae or Cucurbitaceae plant families. However, any other plant or part of a plant which contains the requisite cyclization enzymes are encompassed by the present invention. In relation to engineered cells, these may be plant, animal, insect, fungal, yeast or microbial cells. The cyclization enzyme(s) may be encoded by genetic sequences resident on a plasmid or vector or the genetic sequences may be integrated into the chromosome of the cells. A genetic construct may also be introduced comprising nucleotide sequences encoding an amino acid sequence to the cyclized and the enzyme(s) required for cyclization.

The gene or genes required to encode the cyclization enzymes may be isolated by any number of means including differential display, yeast two hybrid systems, immunological screening techniques and a variety of visual display techniques. In one example, a nucleic acid molecule of the present invention is manipulated to include a nucleotide sequence which encodes a reporter molecule capable of giving an identifiable signal. The reporter gene sequence is inserted into or fused to a nucleotide sequence encoding a precursor form of the cyclotide. Examples of suitable reporter molecules include luciferase and β-galactosidase. The reporter molecule may also encode an amino acid sequence for which an antibody, labelled with a reporter molecule, may interact.

The modified nucleic acid molecule can then be transferred by, for example, transformation, electroporation, conjugation or *Agrobacterium*-mediated transfer to, for example, a bank of cells carrying a genomic library from a plant known to contain the cyclising enzyme or enzymes. When a modified nucleic acid molecule comprising a reporter gene sequence is introduced into a cell comprising the cyclizing enzymes, the precursor sequence is processed and the reporter molecule-encoding portion is cleaved off. As a result, the cells would not produce a detectable signal. Such cells would then be selected for further analysis. *Agrobacterium*-mediated transformation may be via embryonic or organogenic callus.

Many other approaches may be used to screen for and select clones encoding the cyclizing enzymes or to directly identify the enzyme(s). For example, the cyclizing enzyme(s) may be identified using fluoro or colormetric substrates designed based on knowledge of the precursor sequence described herein. In one embodiment, linear peptides are produced which comprise a cleaveable sequence with a colored reagent (e.g. PNA) that would get released and be detectable on treatment with plant-extract containing the enzyme(s). This provides a very powerful selection protocol for plant material containing cyclizing enzyme(s).

Accordingly, another aspect of the present invention contemplates a method of identifying nucleic acid molecules which encode one or more enzymes required for cyclization of an amino acid sequence said method comprising obtaining a nucleic acid molecule which encodes a precursor form of an amino acid sequence capable of being cyclized into a knotted peptide, polypeptide or protein; introducing or fusing to said nucleic acid molecule, a nucleotide sequence which encodes a reporter molecule capable of providing a detectable signal wherein said nucleotide sequence is inserted or fused to a portion of the nucleic acid molecule which is cleaved off prior to or during cyclization; introducing said nucleic acid molecule comprising the nucleotide sequence encoding the reporter molecule into a bank of cells carrying a DNA library comprising all or part of genomic DNA or cDNA from a plant which carries the enzyme or enzymes required for cyclization of an amino acid sequence; screening for and selecting cells which do not synthesize the reporter molecule.

In a preferred embodiment, the plant is from the Rubiaceae, Violaceae or Cucurbitaceae family.

The cyclizing enzyme(s) may also be useful in cyclizing smaller peptides and are useful, for example, in the generation of combinatorial chemistry libraries of small (e.g. 5-30 amino acids) cyclic peptides. These may have a range of applications such as pharmaceutical applications.

The present invention further contemplates a genetically modified cell or cells or a plant or animal comprising said genetically modified cells, said cells comprising a nucleic acid molecule having a nucleotide sequence or complementary nucleotide sequence which encodes an amino acid sequence capable of being cyclized into a knotted peptide, polypeptide or protein. The peptide, polypeptide or protein may be cyclized in vivo or in vitro.

The cells may also be in the form of cells or cell lines or cell cultures.

The present invention permits the manipulation of the nucleic acid molecules to introduce particular functional traits into the cyclized molecules or their linear forms or their precursor forms. A "trait" includes an activity, molecule interacting ability or some other attribute which has the capacity to alter a phenotype. For example, the peptides, polypeptides or proteins may be manipulated to introduce modulating activity of, for example, calcium channel-binding useful in the treatment of pain or a stroke, C5a binding activity useful as an anti-inflammatory agent, proteinase inhibitor activity in plants or animals, antibiotic activity, viral activity (e.g. of HIV or hepatitis virus), microbial activity, fungal activity, cytokine binding and blood clot inhibiting ability amongst other properties.

Alternatively, the cyclic molecules themselves comprise useful traits such as being active against plant pests or pathogens. A plant pest or pathogen includes an insect, arachnid, microorganism, virus and a fungus. The term "pathogen" refers to any biological agent capable of interfering with biological function of said crop plants such that potential agronomic output of said crop plants is reduced.

Accordingly, the present invention contemplates a method of incorporating an amino acid sequence conferring a particular trait into a cyclic peptide, polypeptide or protein, said method comprising fusing or introducing a nucleotide sequence encoding said amino acid sequence to or into a second nucleotide sequence wherein said second nucleotide sequence encodes a peptide, polypeptide or protein which peptide, polypeptide or protein or a derivative therefor is capable of being cyclized into a knotted peptide, polypeptide or protein.

The present invention extends to an antibody that can be used to identify and detect said peptide which is cyclized or not. The invention further extends to the use of the antibody as a primary antibody to detect the said peptide sequence after gel electrophoresis and Western blot transfer.

The present invention comprises a peptide sequence that can be processed from a larger polypeptide sequence. More specifically, the excised polypeptide sequence is flanked by the amino acid sequence triplet GLP at the N-terminal end of the peptide to be cyclized and at the C-terminal end of the peptide to be cyclized. More specifically, the invention refers to a peptide sequence which can be cleaved at the peptide bond immediately prior to either glycine, leucine, proline or valine in either of the GLP sequences flanking the peptide to be excised (see FIG. 8B). All these processing sites are encompassed by the present invention. In particular, the present invention contemplates a range of processing sites which may occur naturally or be introduced. For example, different processing sites may be introduced such that depending on the organelle or tissue targeted, the peptide, polypeptide or protein may be differently processed.

The introduced amino acid sequence is referred to herein as a "heterologous" amino acid sequence.

Another aspect of the invention contemplates an isolated nucleic acid molecule comprising the following nucleotide sequence:

$$[X_1 \ldots X_b[n_1 n_2 \ldots n_a]y_1 \ldots y_c]_d$$

wherein
- $[n_1 n_2 \ldots n_a]$ represents a nucleotide sequence encoding an amino acid sequence capable of being cyclized to a knotted peptide or polypeptide or protein; and
- $X_1 \ldots X_b$ and $y_1 \ldots y_c$ represent polynucleotide sequences capable of encoding an amino acid sequence where a and b and c and d may be any number and when d is >1, the amino acid sequence may be unique for each integer of d.

The nucleic acid molecule according to this aspect of the present invention may be regarded as a hybrid nucleotide sequence comprising the structure:

$$j_1 \ldots j_e[X_1 \ldots X_b[n_1 n_2 \ldots n_a]y_1 \ldots y_c]_d q_1 \ldots q_f$$

wherein
- $[n_1 n_2 \ldots n_a]$ represents a nucleotide sequence encoding an amino acid sequence capable of being cyclized to a knotted peptide or polypeptide or protein;
- $X_1 \ldots X_b$ and $y_1 \ldots y_c$ represent polynucleotide sequences capable of encoding an amino acid sequence where a and b and c and d may be any number and when d is >1, the amino acid sequence may be unique for each integer of d; and
- $j_1 \ldots j_e$ and $q_1 \ldots q_f$ represent nucleotide sequences encoding a peptide, polypeptide or protein capable of directing the peptide, polypeptide or protein to a cellular compartment or organelle where a, b, c, d, e and f may be any number, where d is >1, the amino acid sequence may be unique for each integer of d.

In a related embodiment, there is provided an isolated nucleic acid molecule comprising the following nucleotide sequence:

$$[X_1 \ldots X_b[n_1 n_2 \ldots (k_1 \ldots k_\delta)_\lambda n_a]y_1 \ldots y_c]_d$$

wherein
- $[n_1 n_2 \ldots n_a]$ represents a nucleotide sequence encoding an amino acid sequence capable of being cyclized to a knotted peptide or polypeptide or protein;

$X_1 \ldots X_b$ and $y_1 \ldots y_c$ represent polynucleotide sequences capable of encoding an amino acid sequence where a and b and c and d, δ and λ may be any number and when d or λ is >1, the amino acid sequence may be unique for each integer of d and λ;

$k_1 \ldots k_\delta$ represent a nucleotide sequence encoding an amino acid sequence conferring a particular activity or other trait.

In yet another related embodiment, the present invention is directed to an isolated nucleic acid molecule comprising the following nucleotide sequence:

$$[n_1 n_2 \ldots (n_1^I n_2^I \ldots n_\gamma^I) \ldots n_a]_m$$

wherein $[n_1 n_2 \ldots n_a]$ and $(n_1^I n_2^I \ldots n_\gamma^I)$ represent polynucleotide sequences encoding an amino acid sequence capable of being cyclized to a knotted peptide or polypeptide or protein; and γ and a and m may be any number and when m is >1, the amino acid sequence may be unique for each integer of m.

Further, the invention contemplates an isolated nucleic acid molecule comprising the following nucleotide sequence:

$$j_1 \ldots j_e[X_1 \ldots X_b[n_1 n_2 \ldots (n_1^I n_2^I \ldots (k_1 \ldots k_\delta)_\lambda n_a^I)_m n_a]y_1 \ldots y_c]_d q_1 \ldots q_f$$

wherein $[n_1 n_2 \ldots n_a]$ represents a nucleotide sequence encoding an amino acid sequence capable of being cyclized to a knotted peptide or polypeptide or protein;

$X_1 \ldots X_b$ and $y_1 \ldots y_c$ represents a polynucleotide sequence capable of encoding an amino acid sequence where a and b and c and d and e may be any number and when d is >1, the amino acid sequence may be unique for each integer of d;

$j_1 \ldots j_e$ and $q_1 \ldots q_f$ represents a nucleotide sequence encoding a peptide, polypeptide or protein capable of directing the peptide, polypeptide or protein to a cellular compartment or organelle;

$k_1 \ldots k_\delta$ represents a nucleotide sequence encoding an amino acid sequence conferring a particular activity or other trait;

λ and m and d may be any number and when λ and m and d are each >1, the amino acid sequence may be unique for each integer of λ, m and d.

The "activity" may inter alia be a therapeutic activity, an enzymic activity or an activity useful as a laboratory reagent. Protease inhibitor activities, for example, may be used to generate plants (e.g. crops) resistant to pathogens. Alternatively, protease activities may be used to produce stable molecules useful in industrial grade washing compositions.

In a particularly preferred embodiment, the activity confers protection to a plant or animal cell from pathogen infestation. Examples of pathogens include insects, spiders, and other arachnids, microorganisms, viruses and fungi. Such an activity may also be exhibited by the cyclic peptide, polypeptide or protein without need for the introduction of an additional amino acid sequence. The present invention further extends to linear forms and precursor forms of the peptide, polypeptide or protein which may also have activity or other utilities. Various agricultural applications of the cyclic molecules or their linear forms are particularly contemplated by the present invention. For example, the present invention extends to engineering crop plants (such as cotton) to be resistant to pathogens (e.g. insects).

The present invention further provides genetic constructs comprising the nucleic acid molecules of the present invention. Such a genetic construct is particularly useful for expressing the nucleic acid molecule to produce linear or precursor forms of the cyclizable amino acid sequence. In this case, the genetic construct also comprises one or more promoters operably linked to the nucleotide sequences. Genetic constructs suitable for use in plants are particularly preferred. The genetic constructs may encode linear forms only of the peptides which are then subsequently circularized in vitro using, for example, enzyme(s) or chemical means. Alternatively, cell or cell membrane systems may be employed.

The genetic construct of the present invention may comprise a sequence of nucleotides or be complementary to a sequence of nucleotides which comprise one or more of the following: a promoter sequence, a 5' non-coding region, a cis-regulatory region such as a functional binding site for a transcriptional regulatory protein or a translational regulatory protein, an upstream activator sequence, an enhancer element, a silencer element, a TATA box motif, a CCAAT box motif, an open reading frame, a transcriptional start site, a translational start site, and/or nucleotide sequence which encodes a leader sequence. The genetic construct of the present invention also encodes cyclizable peptide, polypeptide or protein. Furthermore, the genetic construct may comprise a cassette which may be used to insert a nucleotide sequence to be inserted into or fused to a cyclized peptide, polypeptide or protein. Furthermore, the nucleotide sequence to be inserted may consist of polynucleotide units called codons. A codon consists of three nucleotide bases wherein the sequence of the three nucleotide bases defines a specific amino acid. The invention extends to the use of any codon, triplet or polynucleotide sequence known to encode a specific amino acid. Furthermore, the invention extends to any polynucleotide sequence that defines a peptide sequence or polypeptide that can be fused to the inserted sequence for the purpose of targeting, transporting or regulating the expression of the polypeptide sequence to which it is fused. In one particular embodiment, a vacuole or other cellular organelle is targeted.

The term "5' non-coding region" is used herein in its broadest context to include all nucleotide sequences which are derived from an upstream region of an expressible gene, other than those sequences which encode amino acid residues which comprise the polypeptide product of the gene, wherein the 5' non-coding region confers or activates or otherwise facilitates, at least in part, expression of the gene.

The term "gene" is used in its broadest context to include both a genomic DNA region corresponding to the gene as well as a cDNA sequence corresponding to exons or a recombinant molecule engineered to encode a functional form of a product. A gene includes any sequence of nucleotides which may be transcribed into a mRNA molecule. Use of the term "gene" is not to place any structural or functional constraints on the scope of the present invention.

As used herein, the term "cis-acting sequence" or "cis-regulatory region" or similar term shall be taken to mean any sequence of nucleotides which is derived from an expressible genetic sequence wherein the expression of the first genetic sequence is regulated, at least in part, by said sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a structural gene or other nucleic acid molecule, in a cell. Preferred promoters according to the invention may contain additional copies of one or more specific regulatory elements to further enhance expression in a cell and/or to alter the timing of expression of a structural gene to which it is operably connected.

The term "operably connected" or "operably linked" in the present context means placing a structural gene under the regulatory control of a promoter which then controls expression of the gene. Promoters and the like are generally but not necessarily positioned 5' (upstream) to the genes which they control. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting, i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting, i.e., the genes from which it is derived.

The genetic construct(s) of the present invention may be introduced into a cell by various techniques known to those skilled in the art. The technique used may vary depending on the known successful techniques for that particular cell.

Techniques for introducing recombinant DNA into cells such as plant cells include, but are not limited to, transformation using $CaCl_2$ and variations thereof, direct DNA uptake into protoplasts, PEG-mediated uptake to protoplasts, electroporation, microinjection of DNA, microparticle bombardment of tissues or cells, vacuum-infiltration of tissue with nucleic acid, and T-DNA-mediated transfer from *Agrobacterium* to the plant tissue.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 0.1 to 10 μm and more particularly 1 to 5 μm tungsten or gold spheres. The DNA construct may be deposited on the microparticle by any suitable technique, such as by precipitation.

In a particularly preferred embodiment, the nucleotide sequence encoding the cyclizable amino acid sequence or its precursor comprises the amino acid sequence substantially as set forth in <400>2, <400>4 or <400>6 or an amino acid sequence having at least 60% similarity thereto.

Preferably, the nucleotide sequence is substantially as set forth in <400>1, <400>3 or <400>5 or a sequence having at least 60% similarity thereto or capable of hybridizing thereto under low stringency conditions at 42° C.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (7). A detailed discussion of sequence analysis can be found in Unit 19.3 of Ausubel et al. (8).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (9). However, the $T_m$ of a duplex DNA decreases by 1° C. with every increase of 1% in the number of mismatch base pairs (10). Formamide is optional in these hybridization conditions. Accordingly, particularly preferred levels of stringency are defined as follows: low stringency is 6×SSC buffer, 6.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

The present invention further contemplates a genetically modified plant which comprises a nucleotide sequence which encodes an amino acid sequence capable of being cyclized into a knotted peptide, polypeptide or protein and which confers on said plant a trait not present in the same species or variety of plant prior to genetic modification. The plant may also comprise one or more nucleotide sequences which encode one or more cyclizing enzymes.

The genetically modified plants of this aspect of the present invention include plants which are resistant to certain pathogens. Crop plants resistant to pathogens are particularly preferred. Crop plants include but are not limited to cotton, cereal crops, vegetable crops, seed crops and flowering crops.

Yet another aspect of the present invention provides the use of a nucleic acid molecule encoding an amino acid sequence, which amino acid sequence or a derivative or precursor form thereof is capable of being cyclized into a knotted peptide, polypeptide or protein, in the manufacture of a transgenic or genetically modified plant capable of producing said cyclic knotted peptide, polypeptide or protein.

The present invention is further described by the following non-limiting Examples.

EXAMPLE 1

Plant Material

*Oldenlandia affinis* DC and *Viola odorata* were grown under standard glasshouse conditions.

EXAMPLE 2

RNA Isolation

RNA was prepared from various tissues of *O. affinis* using TRIzol (trademark) reagent and the protocol from Gibco BRL (see Gibco BRL form #3796, TRIzol (trademark) Reagent Total RNA Isolation Reagent).

EXAMPLE 3

Methods for Isolating a Partial cDNA Clone Encoding Kalata B1

Single stranded cDNA was prepared from *O. affinis* leaf RNA using the Gibco BRL RT-PCR kit and an oligo-dT primer according to the manufacturer's instructions. The cDNA produced was amplified by the polymerase chain reaction using one of two degenerate primers and oligo-dT (Bresatec). The two degenerate primers and the encoded protein sequence are shown in FIG. 1B. The oligonucleotides were dissolved in milliQ water to a final concentration of 200 µM. The PCR reaction was performed using a profile of 30 cycles of 94° C. (3 min), 37° C. (3 min) and 70° C. (3 min). After 30 cycles, there was a final extension step at 72° C. for 10 min. PCR products were separated on 2% w/v agarose gels in TBE (45 mM Tris Borate, 1 mM EDTA). The QIAGEN Gel extraction kit was used to purify the amplified fragments which were subsequently cloned into the pBluescript SK+ vector (Stratagene) and sequenced by SUPAMAC (Sydney University and Prince Albert Macromolecular Analysis Centre, Sydney, Australia), using T3 and T7 primers.

EXAMPLE 4

Preparation and Screening of the *O. affinis* cDNA Library

Total RNA (1 mg) was prepared from leaves and stem and mRNA was separated using the PolyATract (trademark) I (Promega) mRNA isolation system. Five microgram of mRNA was used to produce the cDNA library in a Lambda-Zap vector using the Stratagene ZAP-cDNA and Gigapack cloning kits according to manufacturer's instructions. The amplified library was screened using a $^{32}$P-labelled DNA fragment corresponding to bases 7-105 of the partial Kalata B1 clone (FIG. 2) as probe. After a second round of screening, hybridizing clones were chosen for sequence analysis. Excised phagemids were transformed into XL1-Blue (Stratagene) *E. coli* cells via electroporation using a GenePulsar electroporation apparatus (BioRad). Plasmid was isolated using the alkaline lysis protocol (11). Sequence analysis was performed by SUPAMAC (Sydney University and Prince Albert Macromolecular Analysis Centre, Sydney, Australia), using T3 and T7 primers. Analysis of DNA sequences was performed using SeqEd (Applied Biosystems). The Oak1 and Oak 2 clones were isolated as described above. The Oak 3 and Oak 4 clones were isolated using an identical procedure except the full length Oak1 cDNA was used as probe.

EXAMPLE 5

RNA Blots

Total RNA (10 µg) was fractionated on 1.2% w/v agarose gels in the presence of formaldehyde and transferred to HyBond N+ (Amersham) as described by Sambrook et al.

(11). Prehybridization (at 42° C.) and hybridization (16 hr at 42° C.) was performed in 5×SSPE (0.9 M NaCl, 50 mM $NaH_2PO_4.2H_2O$, 5 mM EDTA), 1% w/v SDS, 5×Denhardt's solution [0.1% w/v Ficoll, 0.1% w/v BSA fraction V, Sigma], 0.1% w/v polyvinylpyrrolidone, 50% w/v deionised formamide and 100 µg/ml Herring sperm DNA. The membrane was probed with either the Kalata B1 clone (FIG. 2) or the Oak1 cDNA0 (FIG. 4), unbound probe was removed by washing three times with 2×SSC and 1% w/v SDS at 42° C. for 10 min. Hybridizing RNA was visualized after exposure to a phosphoimager screen for 15 hr using a model 400B Phosphorimager (Molecular Dynamics) and ImageQuant (trademark) software.

EXAMPLE 6

DNA Blots

Genomic DNA was isolated from fresh leaf material (1.5 g) as described in the QIAGEN Genomic Tip protocol. Genomic DNA (10 µg) was digested with restriction enzymes; HindIII, BamH1, Ndel and EcoRV (Promega, 5 units) and separated on a 0.7% agarose gel in the presence of ethidium bromide and TBE buffer (11). The DNA was transferred to an $N^+$ nitrocellulose membrane as described (11) and the blot was probed with the full-length Oak1 cDNA. The blot was prehybridized, hybridized and washed as described for the RNA blots. Hybridizing DNA was visualized using a model 400B Phosphorimager (Molecular Dynamics) and ImageQuant (trademark) software.

EXAMPLE 7

Bacterial Expression of the Protein Encoded by Oak1

The cDNA encoding the Kalata B1 precursor protein was PCR amplified from the Oak1cDNA using oligonucleotide primers complementary to bases 61-75 (forward primer) and 361-372 (reverse primer). The amplified fragment was cloned into the pGEM-T-Easy vector (Promega) before it was excised and subcloned into pQE-30 (QIAGEN) to create pQKB1. *Eschericia coli* m15 cells containing the pREP-4 plasmid were transformed with pQKB1 and grown in Luria broth containing ampicillin (100 µg/ml) and kanamycin (12.5 µg/ml) before induction with IPTG (1 mM). Cells were then pelleted by centrifugation and resuspended in sample buffer (12) and heated before analysis by SDS-PAGE. Alternatively, the cells were suspended in a lysis buffer (50 mM Tris-HCl pH 8.5, 2 mM EDTA, 50 µg/ml lysozyme and 10% v/v Triton X-100; 5 ml of lysis buffer/g of cells) before incubation at 37° C. for 15 min. Cell lysate was then mixed with $MgCl_2$ (10 mM final concentration) and DNase 1 (Roche, 10 µg/ml final concentration) and insoluble material was collected by centrifugation (13,000 rpm, 15 min, 4° C.). The insoluble protein pellet was washed several times with 0.5% Triton X-100, 10 mM EDTA before a final wash in distilled water. The proteins in the pellet were dissolved in denaturing lysis buffer (10 mM Tris-HCl pH 8.5, 100 mM NaCl, 8 M urea) before chromatography on an immobilized metal affinity column (TALON (registered trademark) metal affinity resin, Clontech, Palo Alto, Calif., USA) according to the procedure described by the manufacturer for Batch/Gravity-Flow Column Purification (Clontech user manual Protocol #PT1320-1, version #PR96975). Protein eluted from the column was analyzed by SDS-PAGE, RP-HPLC (reversed phase high performance liquid chromatography) or ESMS (electrospray ionization mass spectrometry).

EXAMPLE 8

Reverse Phase High Pressure Liquid Chromatography (RP-HPLC) and Mass Spectrometry RP-HPLC was performed on a Brownlee RP300 C8 analytical column (4.6×100 mm) using a Waters model 510 pump and a Waters model 481 UV detector. Samples were applied in 0.1% v/v trifluoroacetic acid (Buffer A) and were eluted with 60% v/v acetonitrile, 0.089% v/v trifluoroacetic acid (Buffer B) according to a gradient of 0-100% Buffer B over 30 min with a flow rate of 1 ml/min. Eluted protein was detected by absorbance at 215 nm. The molecular mass of the RP-HPLC purified protein was determined by electrospray ionization mass spectrometry (ESMS) using a Perkin-Elmer Sciex API-300 triple quadrupole mass spectrometer fitted with a micro-ionspray ion source.

EXAMPLE 9

Bioassays with Artificial Diets

*Helicoverpa punctigera* larvae were raised on artificial diets based on Haricot beans (Teakle et al. (13)). One liter of diet was composed of 234 g Haricot beans, 14 g agar, 700 ml water, 35 g Tortula yeast, 50 g wheatgerm, 3.5 g ascorbic acid, 1.1 g sorbic acid, 2.2 g p-hydroxybenzoic acid methyl ester, 0.2 g ampicillin, 0.2 g streptomycin, 16 mg prochloraz. The beans were soaked overnight in water, drained and homogenized to a fine paste. Wheatgerm, yeast and 300 ml of water were added. The agar was dissolved in 400 ml of boiling water and added to the mixture. The mixture was cooled to 50° C. before the addition of the remaining ingredients. The blended diet was poured into trays and after setting was used immediately or stored at –20° C. for no longer than two weeks. The test diet was supplemented with the Kalata B1 peptide (0.825 µmol/g of diet). Twenty newly emerged neonates were added to each diet and mortality was recorded every two days. Weight gain was recorded at the sixth day and then every second day thereafter. The larvae were reared in 1.5 ml eppendorfs microfuge tubes (one larva/tube) until day eight when they were transferred to individual plastic containers with lids (Solo (trademark) plastic portion cups, 28 ml) at the eight day. Larvae were fed small amounts of diet (40 mg) initially that was replaced as required to provide a continuous supply. The larvae were kept in a temperature controlled room at 25±1° C., 16:8 (L:D).

*Helicoverpa armigera* larvae were raised on an artificial diet based on cotton leaves. One hundred ml of cotton leaf artificial diet was composed of 3 g cotton leaf powder (see below), 2 g Tortula yeast, 2.4 g wheat germ, 3.2 g ascorbic acid, 0.08 g sorbic acid, 0.16 g paraben (mould inhibitor), 0.08 ml linseed oil, 0.16 ml wheatgerm oil, 0.028 g ampicillin, 0.028 g streptomycin, 3.2 g agar and 80 ml water. Cotton leaf powder was prepared from freshly picked young, healthy cotton leaves which had been rapidly frozen in liquid nitrogen and freeze dried before they were ground to a fine powder using a mortar and pestle. Test diets contained the cyclic Kalata B1 peptide at 0.15% w/v of diet (high kalata) or 0.03% w/v of diet (low kalata), linear peptide (backbone chain opened between residues 7 and 8 [see FIG. 1A] at 0.15% w/v of diet. The control diet contained casein at 0.15% w/v of diet.

The diet was mixed and dispensed as described for the Haricot bean diet and the bioassay was conducted in the same manner.

EXAMPLE 10

Isolation of a Partial cDNA Encoding Kalata B1

Figure 1C:
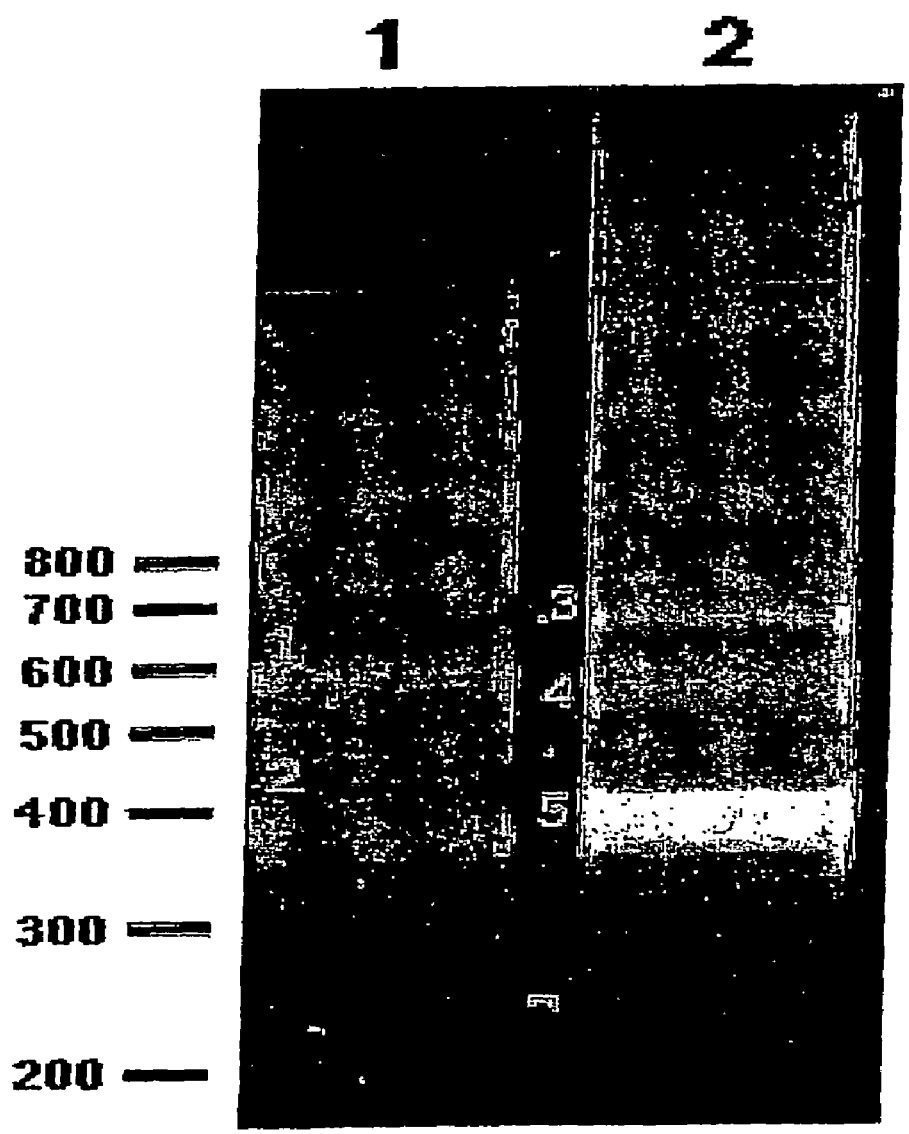

As Kalata B1 is a cyclic protein of only 29 amino acids and the N-terminus was unknown, two degenerate primers were designed to amplify part of the encoding DNA (see FIG. 1). Five PCR amplified products were obtained using these primers in combination with the oligo-dT-HindIII primer (FIG. 1C). The 412 bp fragment produced from primer Kal2 (fragment 5, FIG. 1C) has a 3' untranslated region of 267 bp and a poly A tail of 32 bp together with the complete coding sequence of Kalata B1 (FIG. 2). When used as a probe on RNA blots containing O. affinis leaf RNA, the partial Kalata B1 clone hybridised to an RNA transcript of about 750 bases, suggesting the cyclic peptide is derived from a larger precursor protein (FIG. 3).

EXAMPLE 11

Isolation of a Full Length cDNA Clone for Kalata B1 and a Second cDNA Clone Encoding two Kalata Related Peptides The cDNA library prepared from leaf and stem mRNA was screened using the partial Kalata B1 cDNA as probe. Two fill length clones were obtained, the first designated OaK1 (for *O. affinis* Kalata B1) was 725 bp long and encodes a predicted protein of 124 amino acids (FIG. 4). The 29 amino acid Kalata B1 sequence is embedded in a precursor protein which has a typical endoplasmic reticulum (ER) signal sequence of 20 amino acids. It is likely that the precursor enters the secretory pathway where folding and disulphide bond formation occurs prior to the cyclization and cleavage events that release the mature cyclic peptide. The B1 sequence is preceded by about 70 amino acids at the N-terminus and four to seven amino acids at the C-terminus. All six cysteines in the precursor are located in the B1 sequence. The predicted precursor has no potential N-glycosylation sites and, hence, has an expected mass of 11.18 kDa.

The second cDNA clone, designated Oak2 has an insert of 843 bp and unlike the first clone is predicted to encode two Kalata B1 related sequences which we have called B3 and B6 (FIG. 5). The predicated protein also has typical ER signal sequence of 20 amino acid which is followed by a 46 to 49 amino acid sequence before the first Kalata sequence (B6) is encountered. This peptide is separated from the Kalata B3 sequence by about 25 amino acids. The B3 sequence is flanked four amino acids at the C-terminus (SAAA, SEQ ID NO: 39) which are similar to those which flank B 1 (SLAA, SEQ ID NO: 40) in the protein encoded by the Oak1 clone. Like the precursor encoded by the Oak1 clone, the precursor encoded by the Oak2 clone has no potential N-glycosylation sites and all cysteine residues are confined to the Kalata peptide sequences. After removal of the potential ER signal sequence the precursor encoded by the Oak2 clone has a predicted mass of 14.56 kDa. The size of both clones is consistent with the size of the hybridizing transcript detected in the Northern analysis of leaf RNA (FIG. 3).

The third clone designated Oak3 was 677 bp long (FIG. 6) and encodes a predicted protein of 111 amino acids. It has only one Kalata B1 related sequence that has been called B7.

The fourth clone designated Oak4 has an insert of 993 bp and encodes a predicted protein of 210 amino acids (FIG. 7). This protein has three identical sequences that are related to Kalata B1. This sequence has been called Kalata B2.

A schematic diagram of the precursor proteins predicted from the Oak 1, 2, 3 and 4 clones is given in FIG. 8A. Cyclic peptides with the same sequence as Kalata B1, B2 and B3 have been isolated from the leaves of the *O. affinis* plant (14) (Example 12). The inventors conclude that these peptides are derived by proteolytic cleavage of a precursor protein and formation of a new peptide bond. That is, it is likely that B1, B2 and B3 cyclotides are produced from precursor proteins encoded by the Oak1, Oak4 and Oak2 clones respectively.

Each of the B1, B3, B6 and B7 peptides in the predicted precursor proteins (FIG. 8B) is flanked on both sides by the highly conserved sequence-1-Gly-2-Leu-3-Pro-4-. The circularization process thus involves specific ligation at the same cleavage site within both flanking sequences (one of the four peptide bonds shown) and ligation of the new N- and C-termini. The mature cyclic peptide retains one copy of the Gly-Leu-Pro sequence, which may be derived entirely from one of the original flanking elements, or partially from both depending on the initial cleavage sites (FIG. 8A).

The protein encoded by the Oak4 clone offers further insight into the potential processing site. Unlike the proteins encoded by the other three clones, the Oak4 protein has three copies of a Kalata-like-sequence. This sequence (B2) is flanked by Gly-Leu-Pro at the N-terminus and Ser-Leu-Pro at the C-terminus (FIG. 8B). The B2 peptide isolated from the plant (14) (Example 12) has retained the Gly-Leu-Pro sequence. Processing thus appears to have occurred at the peptide bonds preceding the glycine and the serine (see FIG. 8B).

EXAMPLE 12

Isolation and Structure Determination of Kalata B2

Kalata B2 was isolated from aerial parts of *O affinis* by extraction with dichloromethane/methanol (50:50 v/v) and purified using reverse phase HPLC (Vydac C18 column). Gradients of $CH_3CN$ in $H_2O$ (0.1% trifluoroacetic acid, v/v) were employed in the purification. The purified Kalata B2 was reduced with an excess of tris-carboxyethyl phosphine, TCEP, and alkylated with maleimide. The reduced and alkylated peptide was cleaved with Endo-Glu C in ammonium acetate buffer at pH 7.7 for 2 hours and then purified by reverse phase HPLC. The cleaved peptide was N-terminally sequenced using Edman degradation on an Applied Biosystems 477A Protein Sequencer.

The structure of Kalata B2 was determined using NMR spectroscopy and simulated annealing calculations. Samples for $^1H$ NMR measurement contained ~1.5 mM peptide in 90% $H_2O$/10% $D_2O$ (v/v) at pH 3.6. Spectra were recorded at 290K, 298K and 305K on a Bruker ARX-500 spectrometer equipped with a shielded gradient unit and on a Bruker DRX-750 spectrometer. The following homonuclear 2D NMR spectra were recorded in phase-sensitive mode using time-proportional phase incrementation for quadrature detection in the $t_1$: TOCSY using a MLEV-17 spin lock sequence with an isotropic mixing period of 80 ms; NOESY with mixing times of 200 ms, 250 ms and 300 ms; double quantum filtered DQF-COSY and E-COSY. For DQF-COSY and E-COSY spectra solvent suppression was achieved using selective low-power irradiation of the water resonance during a relaxation delay of 1.8 ms. Water suppression for NOESY and TOCSY experiments was achieved using a modified WATERGATE pulse sequence. Spectra were acquired over 6024 Hz with 4096 complex data points in F2 and 512 increments in the F1 dimension, with 16 to 64 scans per increment. Spectra were processed on a Silicon Graphics Indigo workstation using UXNMR (Bruker) software. The $t_1$ dimension was zero-filled to 2048 real data points and 90° phase-shifted sine bell window functions were applied prior to Fourier transformation. Chemical shifts were referenced to DSS at 0.00 ppm.

Distance restraints were derived from the 250 ms and 300 ms NOESY spectra recorded at 290 K, 298 K and 300 K. Inter-proton distance restraints were assigned upper-distance bounds of 2.70 Å, 3.50 Å or 5.00 Å corresponding to strong, medium or weak cross-peak volumes, respectively. Pseudoatom corrections were applied where necessary to methylene and methyl protons. Backbone dihedral angle restraints were measured from either 1D NMR spectra or the anti-phase cross-peak splitting in a high digital resolution 2D DQF-COSY spectrum. Stereospecific assignment of methylene protons and $X_1$ dihedral angle restraints were derived from coupling constants measured from an E-COSY spectrum in combination with $H_N$—$H_{\beta 2}$, $H_N$—$H_{\beta 3}$, $H_\alpha$-$H_{\alpha 3}$ and $H_\alpha$-$H_{\alpha 3}$ NOE intensities. Slow exchanging amide protons were detected after the sample was lyophilized and reconstituted in 99.99% $^2H_2O$, and were later used to check for consistency of hydrogen bonding interactions in the calculated structures.

Figure 9:
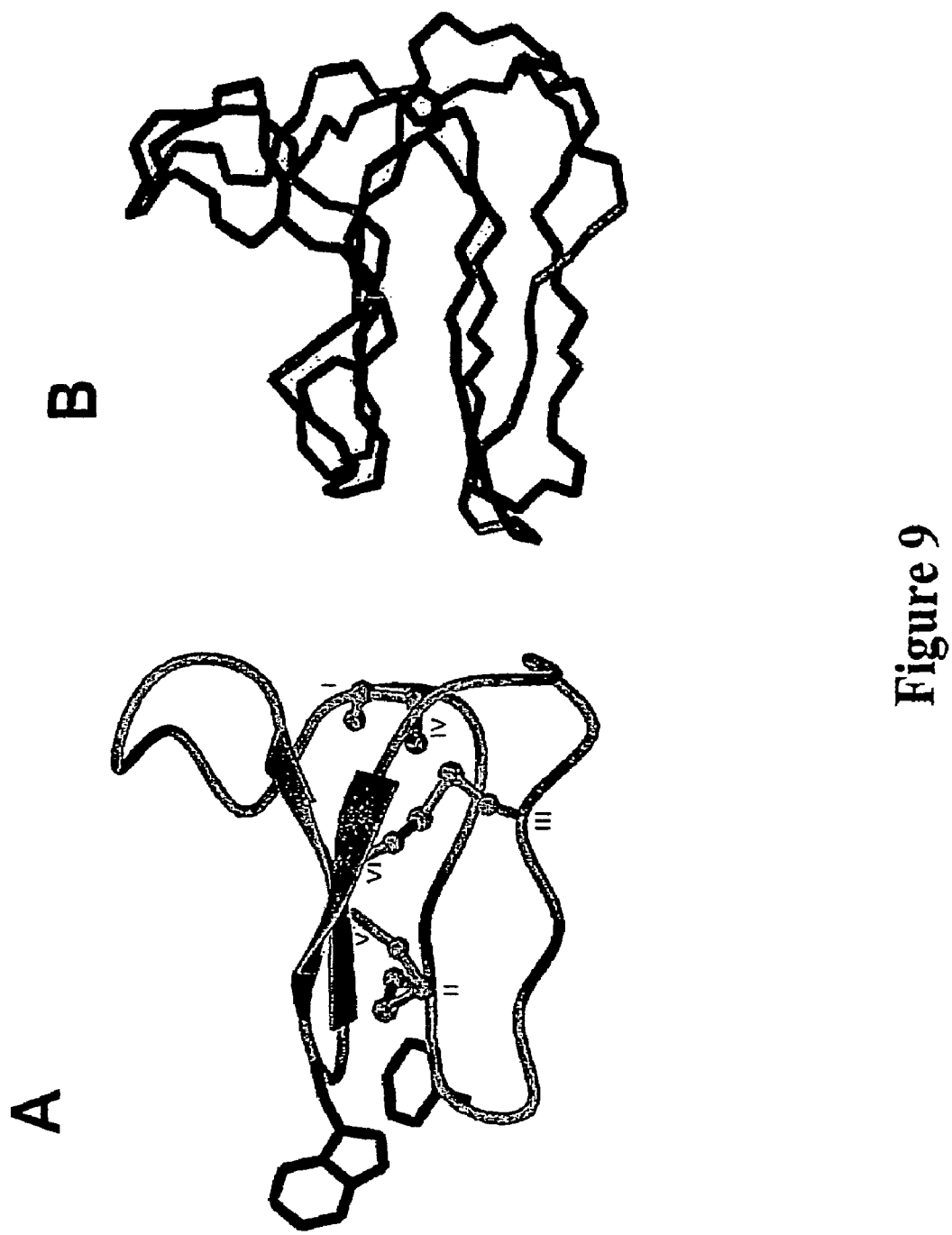
FIG. 9 is a diagrammatic representation showing the structure of Kalata B2 and a comparison with Kalata B1. (A) shows the circular backbone and cross-linking disulfide bonds of Kalata B2. The Cys residues making up these disulfide bonds are labelled I-VI. The arrows represent regions of beta strands. The side chains of two aromatic residues which are located on proximate turns are highlighted. (B) shows a superimposition of the backbone residues of Kalata B2 and Kalata B1 and demonstrates the similarity of their three dimensional structures.

Based on the NMR constraint data the three-dimensional structure of Kalata B2 was calculated using a dynamic simulated annealing protocol in the program X-PLOR version 3.1. The procedure was based on that described by Saether et al., 1995 (1). After an initial simulated annealing calculation of a family of 50 structures the ensemble of structures was checked for violations in NOE restraints and ambiguous cross-peaks were resolved on the basis of inter-proton distances. Finally, each member of the ensemble was energy minimized for 1000 cycles using the conjugate gradient Powell algorithm and a refined force field based on the program CHARMm. A schematic representation of the structure of Kalata B2 is shown in FIG. 9 (left panel). The right panel shows an overlay of the structures of Kalata B1 (1) and Kalata B2.

EXAMPLE 13

Genes Encoding Kalata Like Peptides Belong to a Multigene Family in *O. affinis*

Figure 10:
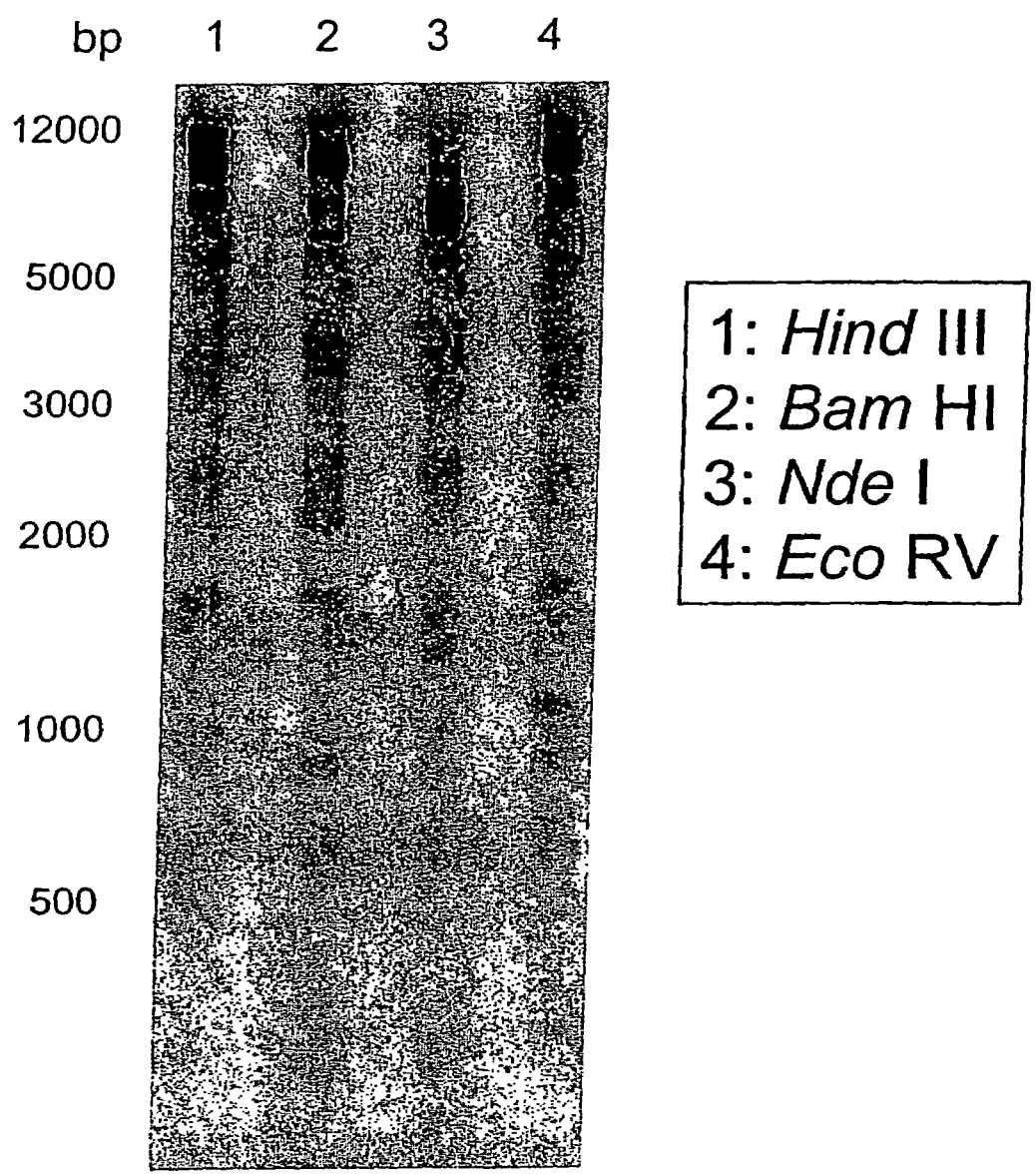
FIG. 10 is a photographic representation of gel blot analysis of genomic DNA from *O. affinis*. Gel blot analysis of genomic DNA digested with HindIII, BamH1, Nde I and EcoRV and probed with radiolabelled Oak1 cDNA (FIG. 4). All enzymes gave at least twelve hybridizing bands. The Oak clones appear to belong to a multigene family with up to twelve members.

Genomic DNA was digested with HindIII, Bam HI, NdeI and EcoRV and subjected to DNA blot analysis using Oak1 cDNA as probe. About twelve hybridizing bands were obtained in all the digests (FIG. 10) suggesting the cyclotides are derived from a multigene family with up to 12 related genes.

EXAMPLE 14

Bacterial Expression of the Kalata B1 Precursor Encoded by the Oak1 Clone

Figure 11A:
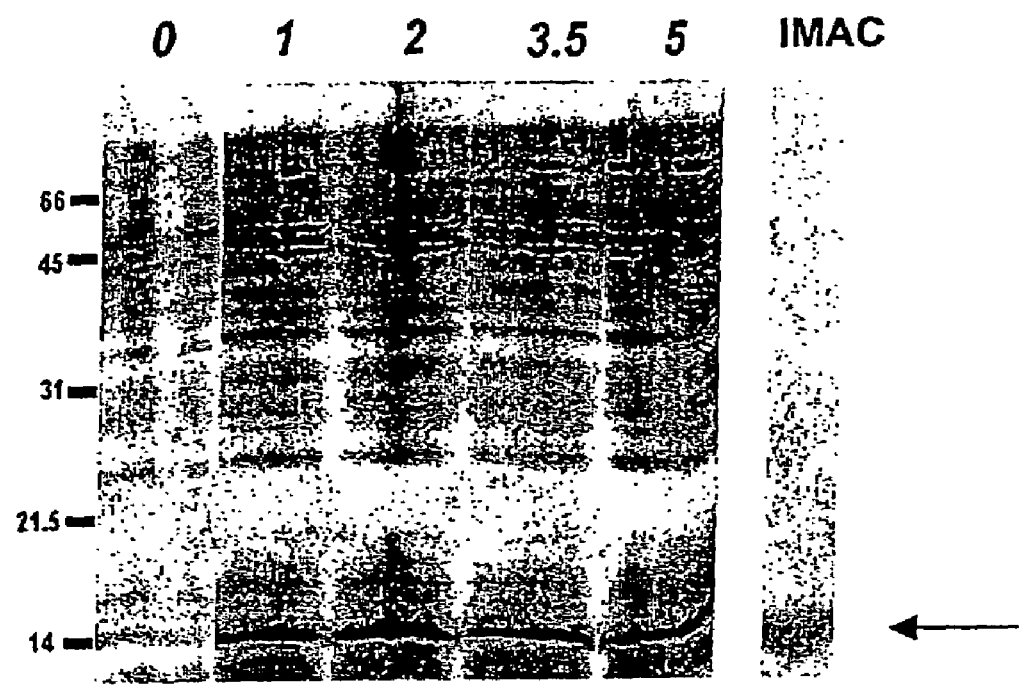
FIG. 11 is a representation showing bacterial expression of the precursor protein encoded by the Oak1 clone. (A) Total cell lysates were prepared at various time points (0-5 hr) post-induction with IPTG by removing 100 µl of cell culture which was lysed in SDS-sample buffer. The proteins were separated on a 12% w/v SDS polyacrylamide gel and stained with silver. A band of approximately the expected size (arrowed) appeared after IPTG induction. Lane numbers indicate hours after induction and broad range kaleidoscope markers (BioRad) were used. IMAC is induced protein purified by immobilized metal affinity chromatography (IMAC). Full-length Oak1 was expressed from the pQE.30 vector in an *E. coli* M15 cell line. B. RP-HPLC of the material that bound to the metal affinity column. The protein in the peak had the same mass as the protein predicted by the Oak1 cDNA together with the hexahistidine tag and henceforth will be called Kalata B1 precursor.
Figure 11B:
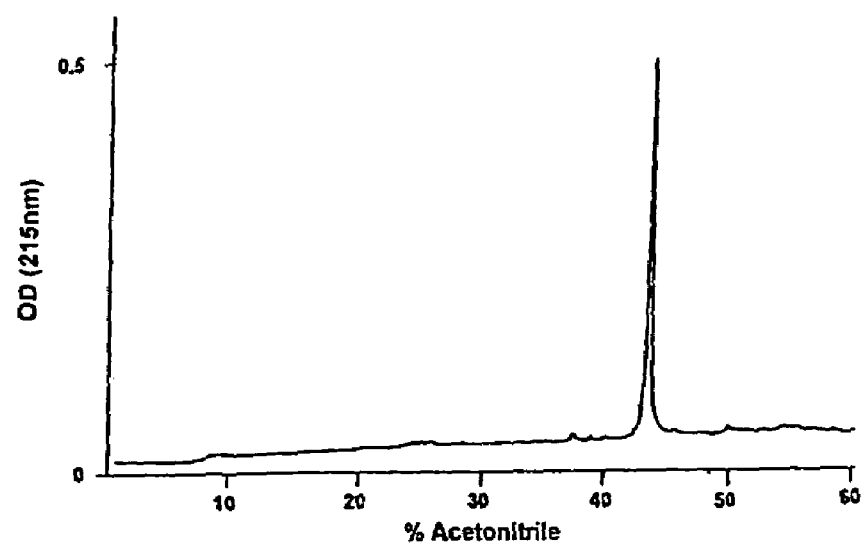

The Oak1 cDNA was subcloned into the pQE-30 vector for bacterial expression. A protein of the expected size was induced after addition of IPTG and was purified by immobilized metal affinity chromatography (IMAC) (FIG. 11). This protein has a mass of 12,938±1.2 Da which is consistent with the predicted mass of the protein encoded by the Oak1 clone together with the hexahistidine tag. Furthermore, the six cysteine residues had formed into three disulphide bonds. The metal affinity purified protein produced a single, sharp peak on reversed phase HPLC (FIG. 11B) indicating that the protein had folded to a single conformation.

EXAMPLE 15

Antibody to the Bacterially Expressed Kalata B1 Precursor Recognizes the Cyclic Peptide The bacterially expressed Kalata B1 precursor (FIG. 11) which had been purified by metal affinity chromatography and reversed phase HPLC (FIG. 11B) was used to immunize a rabbit to generate polyclonal antibodies. The protein (1 mg/ml) in phosphate buffered saline (11) was emulsified with an equal volume of complete Freund's adjuvant (Gibco/BRL) and 100 µg of protein was injected intramuscularly into a rabbit. The first bleed (15 ml) was taken 14 days after injection and serum was collected after incubation of the blood at 37° C. for 1 hr and at 4° C. overnight. The clotted blood was collected by centrifugation (13000 rpm for 20 min at 4° C.) and serum was collected, divided into 200 µl aliquots and stored at −80° C. A booster injection (prepared as described previously except incomplete Freund's adjuvant was used in place of complete Freund's adjuvant) was administered 4, 8 and 12 weeks after the initial injection. Serum prepared from blood collected two weeks after the third boost was used on the immunoblot shown in FIG. 12 at a 1:1000 dilution.

Purified kalata B1 (1 µg), Kalata B1 precursor (1 µg) and buffer soluble proteins from *O. affinis* leaves (100 µg) were subjected to SDS-PAGE on a precast 4-12% bis-tris protein gel (Novex, San Diego, Calif., USA) and transferred to a nitrocellulose membrane 0.2 µm pore size) Micron Separations, Inc., Westborough, Mass., USA) in transfer buffer (48 mM Tris-HCl, 192 mM glycine and 20% [w/v] methanol) by using a Novex transfer apparatus at 100 V for 1 hr at 4° C. After transfer blots were fixed in isopropanol for 1 min followed by 2% w/v glutaraldehyde for 20 min. The blot was then washed for 5 min in TBS (20 mM Tris-HCl and 150 mM NaCl, pH 7.5) before it was blocked by incubation in 5% (w/v) skim milk powder in TBS for 1 hr at room temperature. The blot was rinsed in TBS for 5 min before incubation for 1 hr at room temperature with the primary antibody diluted (1:1000) in TBST (0.1% [v/v] Tween 20 in TBS) containing 5% w/v skim milk powder. The blot was washed again in TBST before the addition of goat anti-rabbit IgG-HRP conjugate (Amersham, 5×10$^{-3}$ dilution in TBST) containing 5% w/v skim milk powder. After 1 hr at room temperature the membrane was washed in TBST and bound HRP was detected by the enhanced chemiluminescence (ECL) detection system of Amersham as described by the manufacturer.

Figures 12A, 12B:
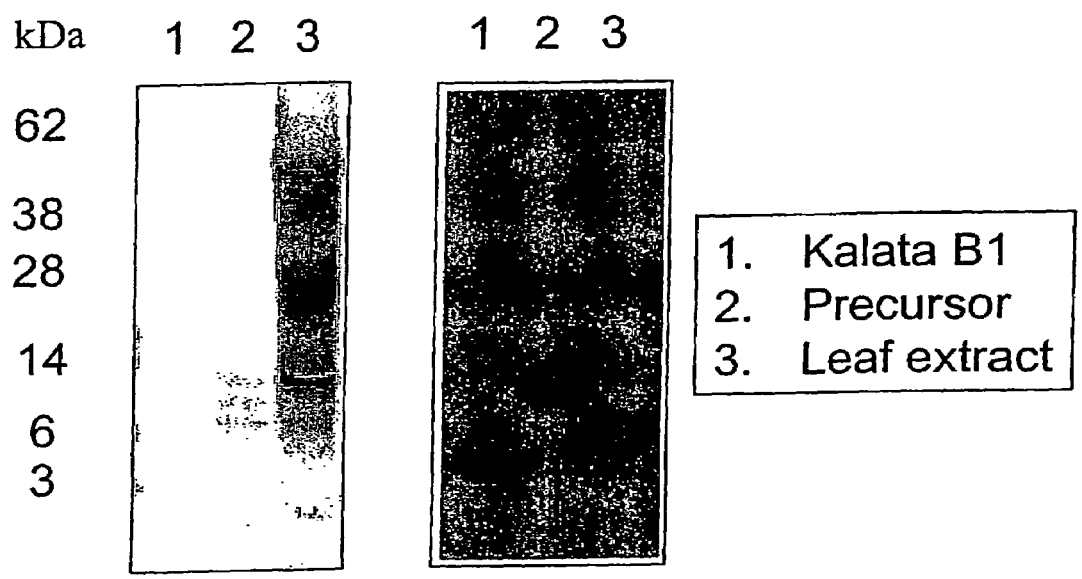
FIG. 12 is a representation showing immunoblot analysis with the antibody raised to the Kalata B1 precursor. (A) Purified kalata B1 (1 µg), Kalata B1 precursor (1 µg) and buffer soluble proteins from *O. affinis* leaves (100 µg) fractionated on a precast 4-12% bis-tris protein gel (Novex, San Diego, Calif., USA) and stained with silver. Markers are the SeeBlue (trademark) Pre-Stained standard from Novex. (B) Proteins in an identical gel after transfer to nitrocellulose (0.2µ) and immunoblotting with antiserum (1:1000) raised against the bacterially expressed Kalata B1 precursor (see FIG. 11). Antibody raised to the Kalata B1 precursor recognizes both the precursor and cyclic Kalata B1.

The antibody raised to the bacterially expressed precursor protein encoded by Oak1 recognized purified Kalata B1 and the bacterially expressed precursor (FIG. 12). This antibody also bound to a peptide with the same mobility as the Kalata B1 cyclotide in buffer soluble extracts from *O. affinis* leaves. This antibody has application in location of the Kalata B1 cyclotide in plant cells and as a tool to monitor processing of the precursor and thus to assist in the identification of processing enzymes.

EXAMPLE 16

Effect of Kalata B1 on the Growth and Development of *H. punctigera* Larvae

Figure 13A:
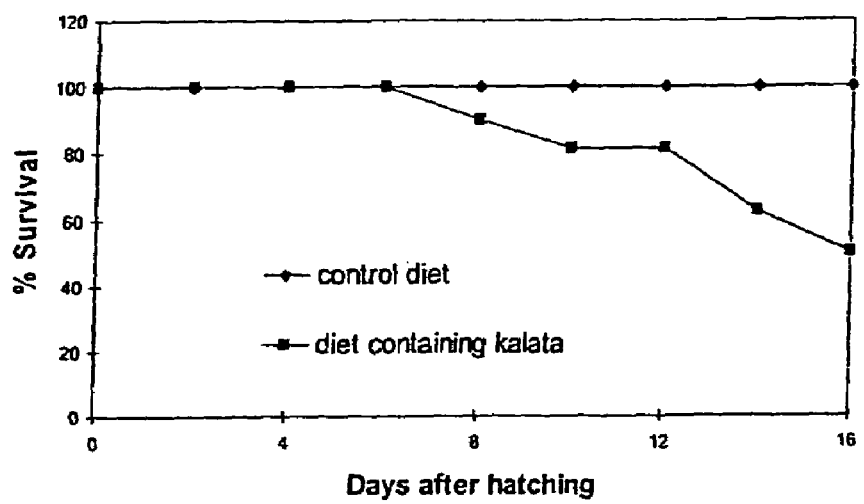
FIG. 13 is a graphical representation showing the effect of Kalata B1 on growth and development of *H. punctigera* larvae. (A) Survival of larvae fed on Haricot bean artificial diet containing Kalata B1 and the control diet. (B) Average mean weight of larvae fed on Kalata B1 and control diet. (C) Size of larvae after 16 days on artificial diet containing Kalata B1 (~5 mm) or control diet (~30 mm).
Figure 13B:
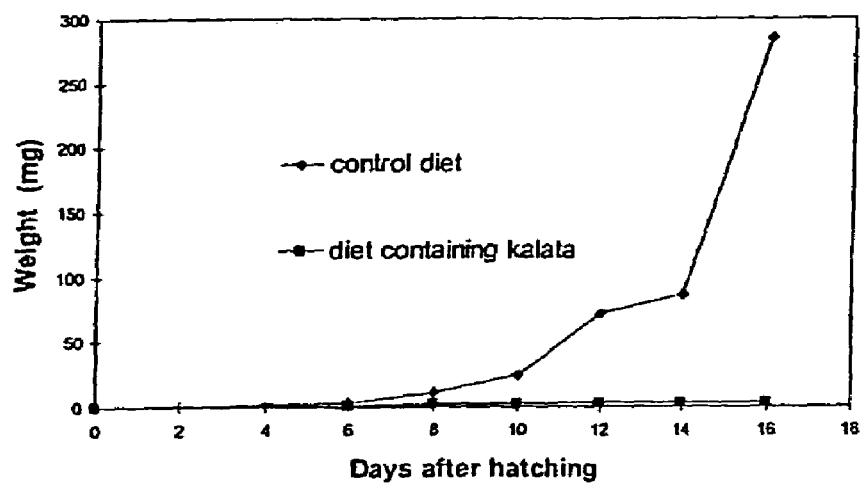
Figure 13C:
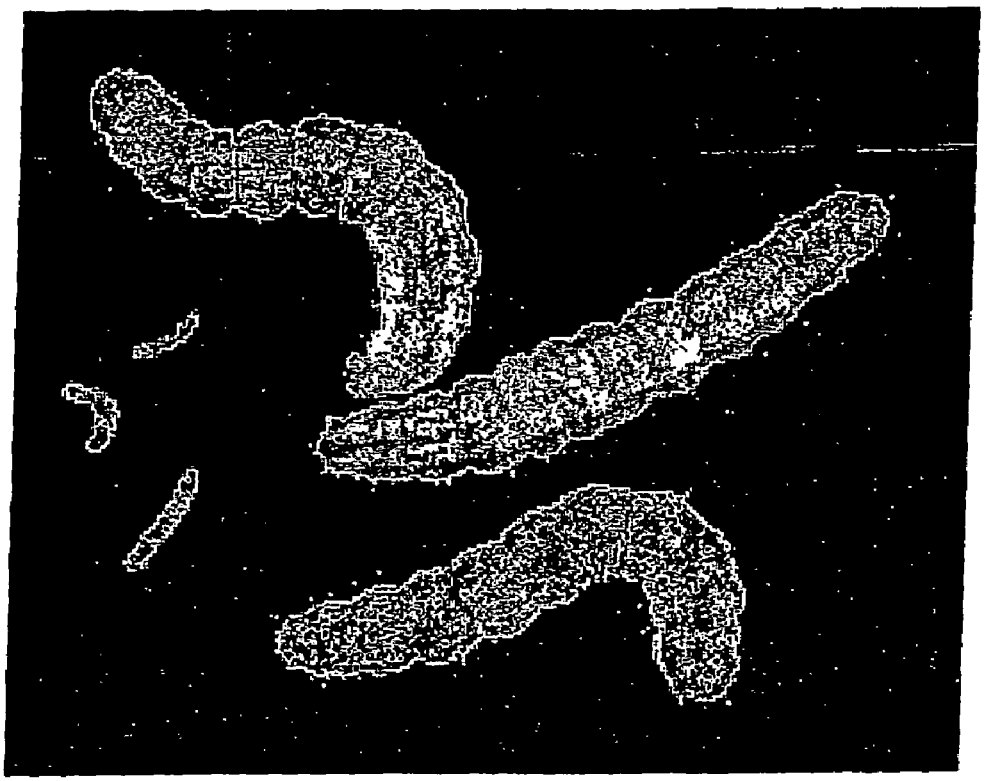
Figure 14A:
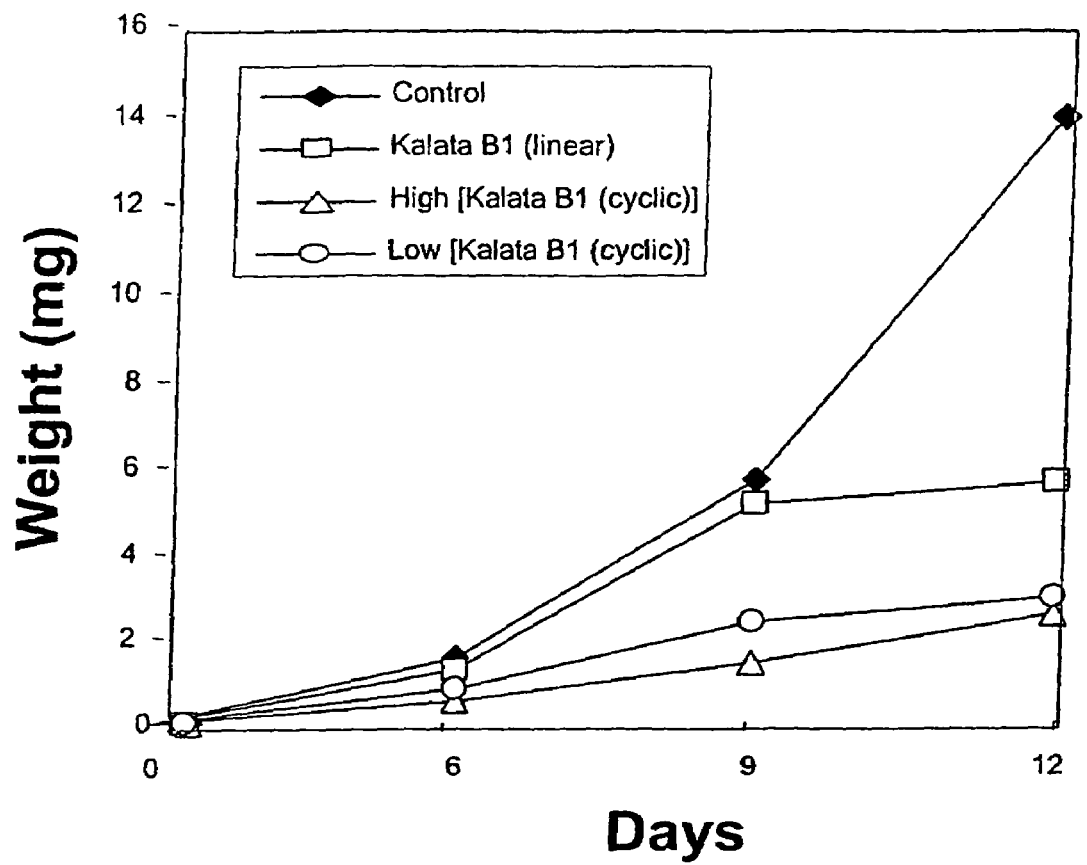
FIG. 14 illustrates the effect of cyclic and linear Kalata B1 on growth of *H. armigera* larvae. (A) Graphical representation of the growth of larvae fed on a cotton leaf artificial diet containing Kalata B1 at 0.15% w/v of diet (high cyclic), Kalata B1 at 0.03% w/v (low, cyclic), linear Kalata B1 at 0.15% w/v or no added Kalata B1 (control). (B) Relative size of larvae after 12 days. 1. Cyclic Kalata B1 (0.15% w/v), 2. Cyclic Kalata B1 (0.03% w/v), 3. Linear Kalata B1 (0.15% w/v), 4. Control.
Figure 14B:
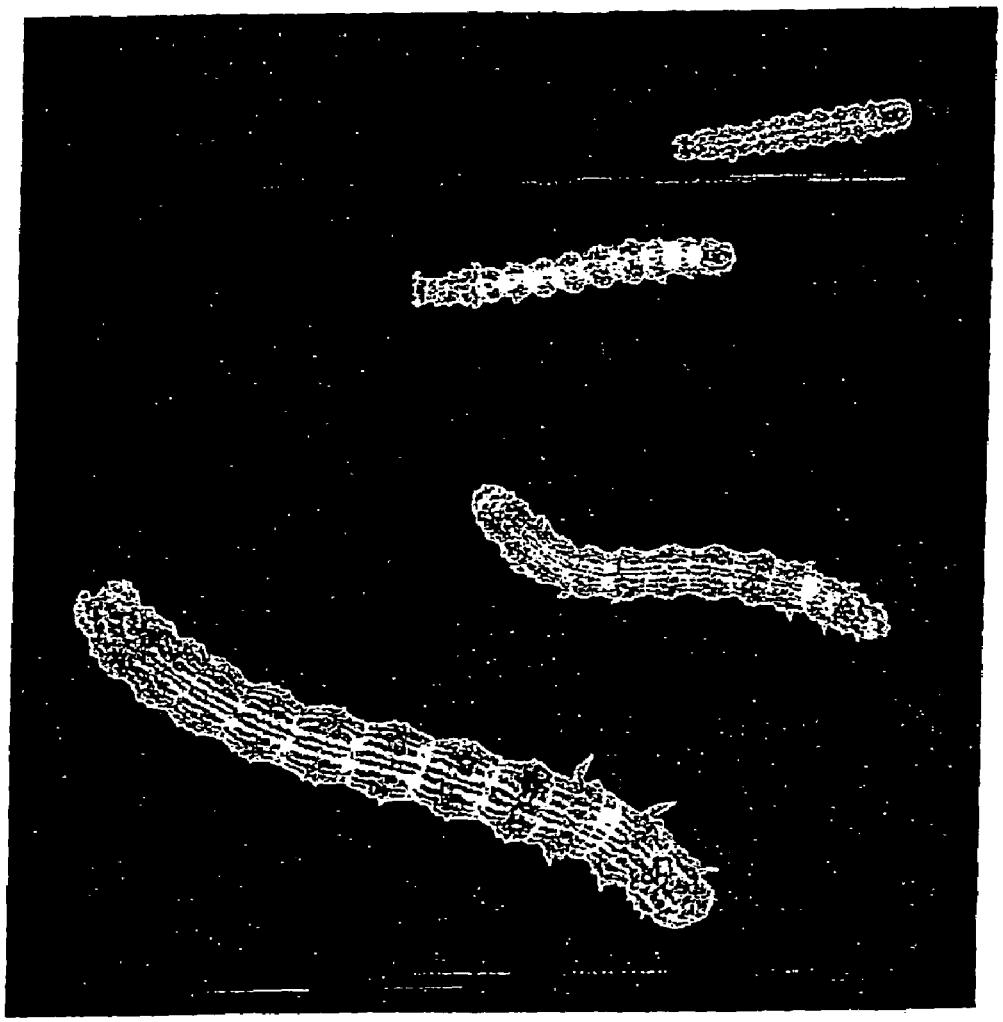

Kalata B1 had a significant effect on the development of larvae. No mortality was observed in the first six days, although 50% failed to survive past day 16 (FIG. 13A). After 16 days none of the 12 survivors had progressed past the first instar stage of development. Most larvae on the control diet, however, had achieved fifth instar (FIGS. 13B, C).

EXAMPLE 17

Effect of Kalata B1 on the Growth and Development of *H. armigera* Larvae

Newly hatched larvae were fed on an artificial diet based on cotton leaves, with and without added Kalata B1. After 12 days on the diet the neonates on the Kalata B1 diet had failed to progress past the first instar stage of development, whereas larvae on the control diet had achieved third to fourth instar. Larvae on the Kalata B1 diet were about 18% of the size of those fed on the control diet.

EXAMPLE 18

Activity of a Linear Form of Kalata B1 in Insect Bioassays

Kalata peptides isolated from leaves are normally cyclic. The inventors sought to determine whether cyclization was essential for biological activity against insects. Newly had been supplemented with cyclic Kalata B1 at either 0.15% w/v of diet or 0.03% w/v of hatched *H. armigera* larvae were added to an artificial diet based on cotton leaves which diet. Growth of these larvae was compared to growth of larvae on diet with no added peptide or with added linear Kalata B1 at 0.15% w/v of the diet. Linear Kalata B1 is identical to cyclic Kalata B1 except the backbone chain is open between residues 7 and 8 [see FIG. 1A].

In contrast to cyclic Kalata B1 the linear form of Kalata B1 had no significant effect on growth for the first nine days of the feeding trial. After 12 days larvae fed on the linear peptide were only about 50% the size of control larvae. The cyclic form of Kalata B1 had a more significant effect on growth even when used at one fifth the concentration of the linear form.

EXAMPLE 19

Cyclotide Genes are Expressed in Roots, Leaves and Stems of *O. affinis*

Figure 16:
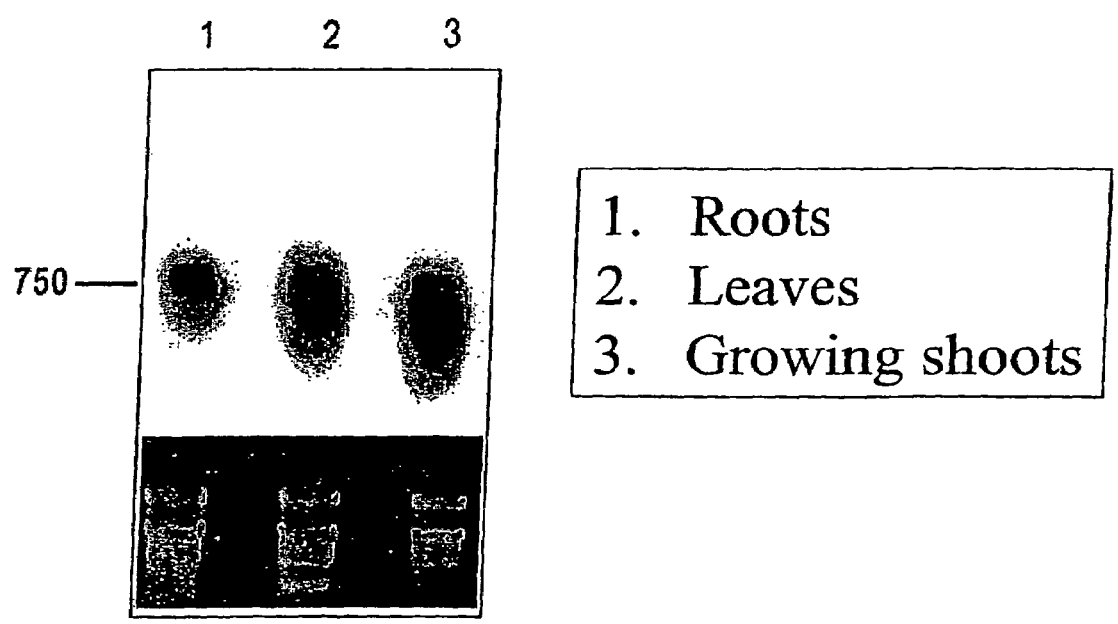
FIG. 16 is a photographic representation showing gel blot analysis of RNA from roots, leaves and stems of *O. affinis*. (A) The RNA blot. The Oak1cDNA (see FIG. 4) hybridized to a broad band of about 750 bases. (B) Identical gel to (A) stained with ethidium bromide to reveal the rRNA bands. Size markers were the 1 Kb Plus DNA Ladder (trademark) from Gibco BRL.

The Oak 1 cDNA was used as a probe on RNA blots containing *O. affinis* root, shoot and leaf RNA. The Oak 1 clone hybridized to RNA transcripts of about 750 bases which are most abundant in leaves and shoots but are also produced by roots (see FIG. 16).

EXAMPLE 20

Cyclotide Genes are Conserved Outside the Rubiaceae

Isolation of a Partial cDNA Encoding a Cyclotide from *Viola odorata*

Viola odorata produces cyclic peptides that are closely related to Kalata B1 and the other cyclotides produced by *O. affinis* (12). The inventors sought to determine whether the genes that encode these peptides are conserved in both *Viola* and *Oldenlandia* species. Single stranded cDNA was prepared from *Viola odorata* leaf RNA and cDNA encoding a cyclic peptide was amplified using the procedure and oligonucleotide primers described in Example 3 for *O. affinis*. A 311 bp fragment was amplified using the Kal2 and oligo-dT-HindIII primers (FIG. 15). This fragment has a 3' untranslated region of 203 bp and a poly A tail of 18 bp. The predicted peptide encoded by nucleotides 1-78 is identical in sequence to 26 of the 29 amino acid residues of Kalata S, a cyclic peptide that has been extracted from Viola odorata plants (12). The three amino acids not covered by this open reading frame are Gly-Leu-Pro. This indicates that the sequence Gly-Leu-Pro is located at the N-terminus of the mature Kalata sequence in the precursor protein encoded by the full length gene. Thus the potential cleavage site in the predicted V odorata precursor occurs before the Glycine at the N-terminus and after the asparagine residue at the C-terminus (last residue in the underlined sequence FIG. 15).

The inventors have shown that cyclotides and their encoding genes are conserved in two plant families, Rubiaceae (*O. affinis*) and Violaceae (*V. odorata*) that come from two taxonomically distinct subclasses (Asteridae and Rosidae) in the eudicot lineage of flowering plants. This suggests that the cyclotide genes may have arisen early in the evolution of flowering plants and are likely to be conserved in other plant families.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Saether et al., *Biochemistry* 34: 4147-4158 (1995).
2. Gustafson et al., *J. Am. Chem. Soc.* 116: 9337-9338 (1994).
3. Witherup et al., *Journal of a Natural Products* 57: 1619-1625 (1994).
4. Schopke et al., *Sci. Pharm.* 61: 145-153 (1993).
5. Claeson et al., *Journal of Natural Products* 61: 77-81 (1998).
6. Goransson et al., *Journal of Natural Products* 62: 283-286 (1999).
7. Altschul et al., *Nucl. Acids Res.* 25: 3389 (1997)
8. Ausubel et al., "Current Protocols in Molecular Biology" John Wiley & Sons Inc, 1994-1998, Chapter 15.
9. Marmur & Doty, *J. Mol. Bio.* 5: 109 (1962).
10. Bonner & Laskey, *Eur. J. Biochem* 46: 83 (1974).
11. Sambrook et al., (1989) Molecular Cloning: A Laboratory Manual, C. Nolan ed. (Cold Spring Harbor, N.Y.; Cold Spring Harbor Laboratories Press).
12. Laemmli *Nature* 227: 680-685 (1970).
13. Teakle et al., *Journal of Invertebrate Pathology* 46: 166-173, (1985).
14. Craik et al., *J. Mol. Biol.* 294: 1327-1336 (1999).

The invention claimed is:

1. An isolated nucleic acid molecule encoding a cyclotide, said nucleic acid molecule comprising the nucleotide sequence set forth in SEQ ID NO:4, SEQ ID NO:13, SEQ ID NO:19 or SEQ ID NO:25.

2. An isolated nucleic acid molecule encoding a cyclotide, said nucleic acid molecule comprising a nucleotide sequence which encodes an amino acid sequence selected from the group consisting of SEQ ID NO:5, SEQ ID NO:14, SEQ ID NO:20 and SEQ ID NO:26.

3. An isolated nucleic acid molecule-comprising a sequence of nucleotides encoding a precursor form of a cystine knot polypeptide operably linked to a heterologous promoter, wherein said cystine knot polypeptide is capable of being cyclized to form a cyclic cystine knot, and wherein the amino acid sequence of said precursor form of said cystine knot polypeptide comprises a signal peptide sequence and the sequence of at least one cystine knot polypeptide, wherein said sequence of at least one cystine knot polypeptide is flanked by amino acid triplets at both the N-terminal and the C-terminal ends of the sequence capable of being cyclized, wherein said amino acid triplets may be the same or different, and wherein the amino acid triplets are selected from the group consisting of GLP and SLP, wherein said sequence of nucleotides encodes a polypeptide comprising an amino acid sequence comprising selected from the group consisting of SEQ ID NO:5, SEQ ID NO:14, SEQ ID NO:20 and SEQ ID NO:26.

4. An isolated nucleic acid molecule comprising a sequence of nucleotides encoding a precursor form of a cystine knot polypeptide operably linked to a heterologous promoter, wherein said cystine knot polypeptide is capable of being cyclized to form a cyclic cystine knot, and wherein the amino acid sequence of said precursor form of said cystine knot polypeptide comprises a signal peptide sequence and the sequence of at least one cystine knot polypeptide, wherein said sequence of at least one cystine knot polypeptide is flanked by amino acid triplets at both the N-terminal and the C-terminal ends of the sequence capable of being cyclized, wherein said amino acid triplets may be the same or different, and wherein the amino acid triplets are selected from the group consisting of GLP and SLP, wherein said sequence of nucleotides comprises a sequence selected from the group consisting of SEQ ID NO:4, SEQ ID NO:13, SEQ ID NO:19, and SEQ ID NO:25.

5. An isolated nucleic acid molecule comprising a sequence of nucleotides encoding a precursor form of a cystine knot polypeptide operably linked to a heterologous promoter, wherein said cystine knot polypeptide is capable of being cyclized to form a cyclic cystine knot, and wherein the amino acid sequence of said precursor form of said cystine knot polypeptide comprises a signal peptide sequence and the sequence of at least one cystine knot polypeptide, wherein said sequence of at least one cystine knot polypeptide is flanked by amino acid triplets at both the N-terminal and the C-terminal ends of the sequence capable of being cyclized, wherein said amino acid triplets may be the same or different, and wherein the amino acid triplets are selected from the group consisting of GLP and SLP, wherein said cystine knot polypeptide is a cyclotide selected from the group consisting of a Kalata B1 polypeptide, a Kalata B2 polypeptide, a Kalata B3 polypeptide, a Kalata B6 polypeptide, and a Kalata B7 polypeptide, and wherein said cyclotide comprises an amino acid sequence selected from the group consisting of SEQ ID NOS:35-38.

* * * * *

UNITED STATES PATENT AND TRADEMARK OFFICE
CERTIFICATE OF CORRECTION

PATENT NO.         : 7,592,433 B1
APPLICATION NO.    : 10/129201
DATED              : September 22, 2009
INVENTOR(S)        : Craik et al.

It is certified that error appears in the above-identified patent and that said Letters Patent is hereby corrected as shown below:

In Columns 53, 54, Claim 3 should read:

"An isolated nucleic acid molecule comprising a sequence of nucleotides encoding a precursor form of a cystine knot polypeptide operably linked to a heterologous promoter, wherein said cystine knot polypeptide is capable of being cyclized to form a cyclic cystine knot, and wherein the amino acid sequence of said precursor form of said cystine knot polypeptide comprises a signal peptide sequence and the sequence of at least one cystine knot polypeptide, wherein said sequence of said of at least one cystine knot polypeptide is flanked by amino acid triplets at both the N-terminal and the C-terminal ends of the sequence capable of being cyclized, wherein said amino acid triplets may be the same or different, and wherein the amino acid triplets are selected from the group consisting of GLP and SLP, wherein said sequence of nucleotides encodes a polypeptide comprising an amino acid sequence selected from the group consisting of SEQ ID NO:5, SEQ ID NO:14, SEQ ID NO:20 and SEQ ID NO:26."

Signed and Sealed this

Tenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,592,433 B1  Page 1 of 1
APPLICATION NO. : 10/129201
DATED : September 22, 2009
INVENTOR(S) : Craik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 728 days.

Signed and Sealed this

Twenty-first Day of September, 2010

David J. Kappos
*Director of the United States Patent and Trademark Office*